(12) United States Patent
Loeb

(10) Patent No.: US 7,527,794 B2
(45) Date of Patent: May 5, 2009

(54) HYBRID PROTEINS WITH NEUREGULIN HEPARIN-BINDING DOMAIN FOR TARGETING TO HEPARAN SULFATE PROTEOGLYCANS

(75) Inventor: Jeffrey A. Loeb, Beverly Hills, MI (US)

(73) Assignee: Wayne State University, Detroit, MI (US)

( * ) Notice: Subject to any disclaimer, the term of this patent is extended or adjusted under 35 U.S.C. 154(b) by 249 days.

(21) Appl. No.: 10/485,206

(22) PCT Filed: Jul. 31, 2002

(86) PCT No.: PCT/US02/24053

§ 371 (c)(1),
(2), (4) Date: Dec. 2, 2004

(87) PCT Pub. No.: WO03/012045

PCT Pub. Date: Feb. 13, 2003

(65) Prior Publication Data

US 2005/0107601 A1    May 19, 2005

Related U.S. Application Data

(60) Provisional application No. 60/308,563, filed on Jul. 31, 2001.

(51) Int. Cl.
*A61K 38/18*    (2006.01)
*C07K 14/435*    (2006.01)
*C07K 14/48*    (2006.01)
*C07K 14/485*    (2006.01)
*C07K 14/50*    (2006.01)

(52) U.S. Cl. .................. 424/185.1; 424/192.1; 530/350

(58) Field of Classification Search ........................ None
See application file for complete search history.

(56) References Cited

U.S. PATENT DOCUMENTS

| 5,367,060 | A |   | 11/1994 | Vandlen et al. |
| 5,665,862 | A |   | 9/1997 | Fischbach et al. |
| 6,037,329 | A | * | 3/2000 | Baird et al. ............... 514/44 |
| 6,096,873 | A | * | 8/2000 | Schaefer et al. ............ 530/399 |
| 6,696,290 | B2 |   | 2/2004 | Fitzpatrick et al. |

FOREIGN PATENT DOCUMENTS

| WO | WO 92/07935 |   | 5/1992 |
| WO | WO 93/22424 A1 |   | 11/1993 |
| WO | WO 97/09051 A1 |   | 3/1997 |
| WO | WO 97/25070 | * | 7/1997 |
| WO | WO 98 19688 |   | 5/1998 |
| WO | WO 98 43649 |   | 10/1998 |
| WO | WO 99/14323 |   | 3/1999 |
| WO | WO 99 55351 |   | 11/1999 |
| WO | WO 00/44736 |   | 8/2000 |

OTHER PUBLICATIONS

Skolnick et al., From genes to protein structure and function: novel applications of computational approaches in the genomic era, Jan. 2000, Trends in Biotech. 18(1): 34-39.*
Park et al, J Biol Chem 276(20): 16611, 2001.*
Wang et al, J Biochemistry 38: 160-171, 1999.*
Mesri et al, J Cell Science 107: 2599-2608, 1994.*
Thomas Meier, et al., "Agrin Can Mediate Acetylcholine Receptor Gene Expression in Muscle by Aggregation of Muscle-derived Neuregulins", The Journal of Cell Biology, May 4, 1998, vol. 141, No. 3, pp. 715-726.
Jeffrey A. Loeb, et al., "Expression Patterns of Transmembrane and Released Forms of Neuregulin During Spinal Cord and Neuromuscular Synapse Development", vol. 126, No. 4, Feb. 1999, pp. 781-791.
Q. Li, et al., "Regulation of Acetylcholine Receptor Genes by Neuregulin-Extracellular Matrix Interactions," Society for Neuroscience Abstracts, vol. 26, No. 1-2, 2000, pp. Abstract No.-26. 10.
Ronit Pinkas-Kramarski, "Differential Expression of NDF/Neuregulin Receptors ErbB-3 and ErbB-4 and Involvement in Inhibition of Neuronal Differentiation," Dec. 4, 1997, vol. 15, No. 23, pp. 2803-2815.
Jeffrey A. Loeb et al., ARIA Can Be Released from Extracellular Matrix through Cleavage of a Heparin-binding Domain, The Journal of Cell Biology, vol. 130, No. 1, Jul. 1995, pp. 127-134.
Jean-Michel Culouscou et al., HER4 Receptor Activation and Phosphorylation of Shc Proteins by Recombinant Heregulin-Fc Fusion Proteins, The Journal of Biological Chemistry, vol. 270, No. 21, May 26, 1995, pp. 12857-12863.
M.A. Marchionni et al., "Neuregulins as Potential Drugs for Neurological Disorders", Cold Spring Harbor Symposia on Quantitative Biology, vol. LXI, 1996, pp. 459-472.

(Continued)

*Primary Examiner*—Phuong Huynh
(74) *Attorney, Agent, or Firm*—Browdy and Neimark, P.L.L.C.

(57) ABSTRACT

Polypeptides of the neuregulin (NRG) heparin binding domain (N-HBD) and nucleic acids coding therefor are disclosed. In particular, fusion polypeptides are produced that comprise, as a targeting structure, a N-HBD polypeptide, fragment, homologue or functional derivative and a protein to be targeted. This is fused to a polypeptide or peptide being targeted (Ptrg) to cell surfaces rich in heparan sulfate proteoglycans to either activate or inhibit interactions at tyrosine kinase receptors. Such products are used to treat diseases or conditions where either agonism or antagonism at tyrosine kinase receptors has beneficial effects, including cancer and a multitude of diseases of the nervous system.

12 Claims, 8 Drawing Sheets

OTHER PUBLICATIONS

Swanston-Flatt et al., "Glycaemic Effects of Traditional European Plant Treatments for Diabetes, Studies in Normal and Streptozotocin Diabetic Mice", Diabetes Research, Teviot-Kimpton Publication, vol. 10(3):69-73, (1989).

Database, Abstract, Section Ch, Week 200132, Derwent Publications Ltd., Wang, (Jan. 31, 2001).

Okada et al., "Effect of Methylcobalamin on Diminished Motor Nerve Conduction Velocity in the Tibial Nerve of Poorly Controlled Diabetics", Clinical Trials Journal, Elsevier, Amsterdam, NL, vol. 22(6):534-536, (1985).

Database, Abstract, Section Ch, Week 198421, Derwent Publications Ltd., Armansow, (Mar. 12, 1984).

Cameron, et al., "New Therapeutic Approaches to Prevent or Halt the Progression of the Long-Term Complications of Diabetes Mellitus: Focus on Neuropathy," Current Opinion in Oncologic, Endocrine and Metabolic Investigational Drugs, Current Drugs, vol. 2(2):162-177, (2000).

* cited by examiner

HYBRID PROTEINS WITH NEUREGULIN HEPARIN-BINDING DOMAIN FOR TARGETING TO HEPARAN SULFATE PROTEOGLYCANS

BACKGROUND OF THE INVENTION

1. Field of the Invention

The invention in the field of biochemistry and neurosciences relates to compositions and methods based on the neuregulin heparin binding domain (N-HBD) use to target other polypeptides to cell surfaces and extracellular matrix rich in heparan sulfate proteoglycans (HSPGs) for the treatment of cancer or various nervous system diseases.

2. Description of the Background Art

In order to carry out their diverse physiological functions, cells must adhere to cellular and extracellular components of their environment in a specific manner. Adherence-requiring functions in the nervous system include neurite extension, synapse formation and axon myelination. The ability to recognize multiple environmental cues and undergo specific adhesive reactions is critical to such complex cellular functions. Recognition and adhesion are mediated by cell adhesion molecules ("CAMs") which bind to macromolecules expressed on neighboring cells or in the extracellular matrix ("ECM").

Three motifs present in adhesion molecules for which 3D structure is known are: immunoglobulin (Ig) superfamily domains, fibronectin type III (Fn-III) domains and the domains found in cadherins. In the nervous system, Ig superfamily members mediate Ca-independent homophilic and heterophilic binding. The extracellular regions of these molecules include one or more domains with sequence similarity to variable (V) or constant (C) domains of antibodies, i.e., Ig's (Williams, A F et al., *Annu. Rev. Immunol.* 6:381-405 (1988). Yoshihara, Y et al., *Neurosci. Res.* 10:83-105 (1991). Many Ig superfamily molecules consist of tandem Ig-like domains bonded in series with multiple copies of a second building block domain (e.g., an Fn-III repeat). Because two molecules that share detectable sequence similarity have been found to adopt the same folding topology, investigators have used structures of molecules discovered in studies of the immune system as "first order" models for the structures of Ig domains in neural CAMs.

These molecules, in particular Ig-like domains, and their topology are reviewed in detail in Vaughn D E et al., *Neuron* 16:261-273 (1998), which is incorporated by reference in its entirety. Ig V domains are the prototype of the V-like domains of CAMs and their type of fold is found in antibody $V_H$ and $V_L$ domains and the N-terminal domains of the T cell receptor α Vaughn et al., supra, V-like domains are found in T cell surface molecules CD4 (first and third domains) and CD8, the N-terminal domains of the "immune system CAM" CD2, vascular cell adhesion molecule-1 (VCAM-1) and telokin, and the C-terminal domain of the myosin light chain kinase. Ig C1 domains consist of seven B strands arranged into two antiparallel sheets. The two sheets are connected by a disulfide bond between strands "B" and "F." In an antibody, constant domains are found in the Fc regions and the C-terminal domains of the Fab Ig fragment. Constant-like or C1 set domains, are also found in the membrane proximal domains of MHC molecules and T cell receptors. The C2 and C1 folding topologies are similar, except for the "sheet switching" of one β strand and the fact that β strands in Ig C2 domains are somewhat shorter (~6 vs ~9 residues) and lack many of the conserved sequence patterns at the N-terminal end of the β barrel. According to Vaughn et al., supra, C2 domains are present in three Ig superfamily members: CD2, the second domain of VCAM-1 and the second and fourth domains of CD4. The heparin binding domain of neuregulin, which is at the center of the present invention, is an Ig-C2 domain.

An important means of intercellular communication is the release of growth and differentiation factors from one cell and their binding to and activation of membrane receptors on a nearby cell which ultimately changes its properties through changes in gene expression. Once released, many polypeptide factors have additional binding interactions with heparan-sulfate proteoglycans (HSPGs) situated in the ECM between cells. The functional consequences of this dual-binding interaction are not entirely clear, but may serve to concentrate these factors at sites where they are needed, to protect them from proteolysis, and to modulate their interactions with their receptors (Schlessinger, J. et al., (1995) *Cell* 83, 357-360). What is even less clear, is how these extracellular interactions modulate the intracellular events that ultimately change a cell's properties.

The neuregulins (NRGs) are a family of heparin-binding growth and differentiation factors with multiple functions in (a) growth and development of the nervous system and heart, and (2) cancer (Fischbach, G. D. et al. (1997) *Annu Rev Neurosci* 20, 429-458). NRGs are released from motor nerve endings at neuromuscular synapses and activate members of the epidermal growth factor (EGF) family of tyrosine kinase receptors, erbB2, erbB3 and erbB4, in the postsynaptic muscle membrane (Loeb, J A et al., (1999) *Development* 126, 781-791; Goodearl, A D et al., (1995) *J Cell Biol* 130, 1423-1434; Moscoso, L M et al., (1995) *Developmental Biology* 172, 158-169; Zhu, X et al., (1995) *EMBO Journal* 14, 5842-5848). This trans-synaptic activation results in a dramatic up-regulation of muscle acetylcholine receptors (AChRs) needed to guarantee proper synaptic transmission. NRG also promotes the transition from embryonic to adult forms of mammalian AChRs by inducing the switch to the α-AChR subunit (Martinou, J C et al., (1991) *Proc. Natl Acad Sci USA* 88, 7669-7673) and the expression of voltage-gated sodium channels (Corfas, G et al., (1993) *Journal of Neuroscience* 13, 2118-2125). All of these effects are expected to increase the efficacy of synaptic transmission as the target muscle fiber increases in size and the neuromuscular junction matures. Consistently, mice in which the Type I NRG1 allele is disrupted by homologous recombination, exhibit (1) a 50% reduction in the density of postsynaptic AChRs, and (2) a reduced safety factor for neuromuscular transmission when challenged by low doses of curare (Sandrock, A W et al. (1997) *Science* 276, 599-603).

A common feature shared by all NRGs is an epidermal growth factor-like (EGF-like) domain. Even when expressed by itself, this domain is sufficient for receptor binding and activation of homo- and heterodimers of erbB2, erbB3, and erbB4 receptors which are highly concentrated at the neuromuscular synapses in the postsynaptic muscle membrane (Moscoso et al.,supra; Xu et al., supra; Altiok, N. et al., v (1995) *Embo J* 14, 4258-4266). The rapid autophosphorylation of Tyr residues in these receptors initiates a signaling cascade that translates the initial binding event into the induction of AChR genes (Corfas, G. et al., (1993) *Proc. Natl Acad Sci USA* 90, 1624-1628). This signaling cascade involves a number of signaling pathways including both the mitogen-activated protein (MAP) kinase (Si, J. et al., Luo, Z., and Mei, L. (1996) *J Biol Chem* 271, 19752-19759; Tansey, M G et al., (1996) *J. Cell Biol* 134, 465-476; Altiok, N et al., (1997) *EMBO Journal* 16, 717-725) and phosphatidyl-inositol 3-kinase (PI3K) pathways (Si et al., supra).

Most spliced forms of NRG also have an immunoglobulin-like (IG-like) domain N-terminal to the EGF-like domain (FIG. 1). Because this domain is a heparin-binding domain ("HBD") it is referred to herein as the neuregulin HBD (or "N-HBD"). The terms "IG-like domain" (from NRG) and "N-HBD" are meant to be interchangeable.

The present inventor and others have shown that this domain interacts with HSPGs and may lead to the deposition of NRGs in the ECM of neuromuscular synapses and within the central nervous system (Loeb et al., supra; Loeb, J A et al., (1995) *J Cell Biol* 130, 127-135; Meier, T., et al., (1998) *J Cell Biol* 141, 715-726). HSPGs, including agrin, have been identified to play important roles in neuromuscular junction formation (Sanes, J R et al., (1999) *Annu Rev Neurosci* 22, 389-442).

HSPGs may serve to "direct" the accumulation of NRG forms that include the N-HBD to the basal lamina of developing neuromuscular synapses and to other locations in the developing nervous system at key stages of development (Loeb et al., 1999, supra). The functional consequences of NRG-HSPG interactions on AChR expression, however, are not known.

One feature of NRG that distinguishes it from other heparin-binding ligands is that it has distinct domains for heparan sulfate binding and receptor binding that are separated from one another by a glycosylated spacer region. Recognition of this fact led the present inventor to determine the direct effects of HSPG binding on receptor- and gene activation that would not be readily possible with other heparin-binding ligands.

Rio, C et al., *Neuron* 19:39-50 (1997) described a 27 amino acid peptide of chick NRG that corresponded to the HBD. This peptide was made only for use as an immunogen for producing an antiserum in rabbits.

Loeb, J A et al., 1995, supra, speculated that immobilization of NRGs to the ECM might be via their Ig-like domains binding to HSPGs. This was derived indirectly from the observation that heparin inhibited post-binding receptor tyrosine phosphorylation caused by recombinant NRGs.

Since NRGs bind to heparin (Falls, D L et al., 1993, *Cell* 72:801-815), Meier T et al., *J Cell Biol*, 1998, 141:715-726, examined whether recombinant HRG (=NRG) cloned from a human cDNA library bound directly to recombinant chick agrin (a HSPG) by the negatively charged glycosaminoglycan (GAG) side chains as proposed by Loeb et al., supra. It was found that the Ig-like domain of NRGs mediated binding to these GAG chains. To test whether interaction of NRGs with components of the synaptic ECM could be mediated by the Ig-like domain, the investigators expressed a truncated HRG protein containing the Ig-like domain, HRGΔBbsI and discovered that the Ig-like domain, but not the EGF-like domain, bound to agrin.

While there have been numerous disclosures of Ig-C regions or various parts of Ig molecules fused to other proteins for various purposes, these primarily derived from true Ig molecules. The N-HBD of the present invention has less than 40% homology or sequence similarity to these true Ig domains so as to be distinct structurally and functionally from those in the prior art. Examples of such disclosures include the following.

U.S. Pat. Nos. 5,116,964 and 5,428,130, (Capon, et al) disclose a nucleic acid encoding a polypeptide fusion comprising a ligand binding partner protein containing more than one polypeptide chain one of which may be fused to an Ig C region through C-terminal carboxyl or the N-terminal amino groups. The lectin domain described in these documents, which is completely distinct from the NRG-HBD neuregulin IG domain of the present invention, is said to target active peptides to cell surfaces. Moreover, such targeting is not directed to, nor specific for, heparan sulfates at the cell surfaces. U.S. Pat. No. 5,565,335 (Capon, et al.) describes an "immunoadheson" comprising a fusion protein in which a polypeptide making up the adheson variable (V) region is fused at its C-terminus to the N-terminus of a polypeptide comprising an Ig C region.

U.S. Pat. Nos. 6,018,026 and 5,155,027 (Sledziewski et al.) describe biologically active polypeptides (and their coding DNA), and, specifically, dimerized fusion products comprising a first and a second polypeptide chain, each of which comprises a non-Ig polypeptide and requires dimerization for biological activity, joined to a dimerizing protein of heterologous origin relative to the non-Ig polypeptide. Also described is a polypeptide chain of the non-Ig polypeptide dimer, joined to at least one Ig H chain C region domain ($C_H1$, $C_H2$, $C_H3$ or $C_H4$. The expressed, dimerized fusion polypeptide exhibits biological activity characteristic of the non-Ig polypeptide dimer.

U.S. Pat. No. 5,541,087 (Lo, et al.) describes DNA encoding a fusion protein comprising a polynucleotide encoding an Ig Fc region which lacks at least the $C_H1$ domain and a target protein sequence. U.S. Pat. No. 5,869,046 (Presta, et al.) discloses a method for preparing a variant "polypeptide of interest" which is an Fab or a (Fab')$_2$ fragment, the Ig domain (or an Ig-like domain) of which comprises at least one of a $C_H1$ or $C_L$, region. U.S. Pat. No. 6,121,022 (Presta, et al.) discloses a modified polypeptide having an Ig C domain or an Ig-like C domain and an epitope that binds to a salvage receptor within the Ig- or Ig-like C domain. This epitope, absent from the unmodified polypeptide, is taken from two loops of the $C_H2$ domain of an Ig Fc region. The Ig-like domains described in these documents are clearly distinct from the N-HBD of the present invention.

U.S. Pat. No. 6,121,415 describes a family of polypeptides, collectively called neuregulins (NRG1) that appear to result from alternate splicing of a single gene which was mapped to the short arm of human chromosome 8 by Orr-Urtreger et al (1993) *Proc. Natl. Acad. Sci. USA* 90:1867-1871. The NRG3s (murine and human) were disclosed as being about 713 and 720 amino acids in length, respectively, and to comprise an EGF-like domain, an N-terminal hydrophobic segment, the serine/threonine-rich portion, a predicted transmembrane domain, and a predicted intracellular domain.

Three documents by Holmes et al. (*Science* 256:1205-1210 (1992); WO 92/20798; and U.S. Pat. No. 5,367,060) describe isolation and cloning of a family of polypeptide activators for the HER2 receptor which they called heregulin-α (HRG-α), heregulin-β1 (HRG-β1), heregulin-β2 (HRG-β2), heregulin-β2-like (HRG-β2-like), and heregulin-β3 (HRG-β3). These documents describe (1) the ability of the purified HRG (=NRG) polypeptides to activate tyrosine phosphorylation of the HER2 receptor in MCF7 breast tumor cells and (2) the mitogenic activity of the HRG polypeptides on tumor cells expressing high levels of the HER2 receptor. Like other EGF family growth factors, soluble HRG polypeptides appear to be derived from a membrane bound precursor (pro-HRG) which is proteolytically processed to release the 45 kDa soluble form. Although substantially identical in the first 213 amino acid residues, the HRGs are classified into two major types, α and β, based on two variant EGF-like domains which differ in their C-terminal regions. Based on an amino acid sequence comparison, Holmes et al., supra found that between the first and sixth cysteines in the EGF-like domain, HRGs were 45% similar to heparin-binding EGF-like growth factor (HB-EGF), 35% identical to amphiregulin, 32% identical to TGF-α, and 27% identical to EGF.

Falls et al. (1993) *Cell* 72:801-815 described another heregulin family member which termed "acetylcholine receptor inducing activity" (ARIA) polypeptide. The chicken-derived polypeptide stimulated synthesis of muscle AChR s. See also WO 94/08007. ARIA is a β type HRG and lacks the entire spacer region rich in glycosylation sites between the Ig-like domain and EGF-like domain of HRGα, and HRGβ1-β3.

Marchionni et al. (1993) *Nature* 362:312-318, identified several bovine-derived proteins named glial growth factors (GGFs) which share the Ig-like domain and EGF-like domain with the other NRG/HRG proteins described above, but also have an amino-terminal kringle domain. See also WO 92/18627; WO 94/00140; WO 94/04560; WO 94/26298; and WO 95/32724.

Ho et al.(1995) *J. Biol. Chem.* 270:14523-14532, described another member of the HRG family called sensory and motor neuron-derived factor (SMDF) which has an EGF-like domain characteristic of all other HRG polypeptides but a distinct N-terminal domain. The major structural difference between SMDF and the other HRG polypeptides is the lack of an Ig-like domain and the "glyco" spacer characteristic of all the other HRG polypeptides.

Caraway et al. (1994) *J Biol Chem.* 269):14303-14306 subsequently demonstrated that ErbB3 is a receptor for HRG and mediates phosphorylation of intrinsic tyrosine residues as well as phosphorylation of ErbB2 receptor in cells which express both receptors. HRG was the only known member of the EGF-like family that could interact with several receptors (Carraway et al. (1994) *Cell* 78:5-8.

A number of biological activities of the NRG/HRG proteins have been described:
(1) myotube differentiation by acting on synthesis and concentration of neurotransmitter receptors in the postsynaptic muscle (Falls et al., supra);
(2) increased number of sodium channels in chick muscle (Corfas et al., (1993) *J. Neuroscience* 13:2118-2125);
(3) mitogenic stimulation of subconfluent quiescent human myoblasts and their differentiation to yield more myotubes (Sklar et al. (1994) *J. Cell Biochem.* Abstr. W462, 18D, 540); and WO 94/26298, Nov. 24, 1994); and
(4) NRG1, expressed in endocardium, is an important ligand required for activation of myocardial ErbB2 and ErbB4 receptors (Ford, B D et al., *Dev Biol.* (1999) 214:139-150; Carraway, K L et al., *Bioessays* (1996) 18:263-266.

SUMMARY OF THE INVENTION

Some of the ABBREVIATIONS used herein include: NRG, neuregulin; NRG, heregulin; HBD, heparin-binding domain; N-HBD, neuregulin heparin-binding domain; AChR, acetylcholine receptor, HSPG, heparan-sulfate proteoglycan; EGF, epidermal growth factor; IG or Ig, immunoglobulin; MAPK, mitogen-activated protein kinase; PI3-K, phosphatidylinositol 3-kinase; BSA, bovine serum albumin; MEM, minimum essential media; CEE, chick embryo extract; α-BTX, α-bungarotoxin; FGF, fibroblast growth factor; ECM, extracellular matrix; TGF-β transforming growth factor-β; CREB, cAMP response element-binding protein.

The present inventor has discovered that the N-HBD (also referred to as the neuregulin IG-like domain) functions to keep the EGF-like domain at sufficiently high concentrations near erbB receptors for a sufficiently long period of time necessary to induce events downstream from—receptor binding such as AChR gene expression. The present inventor examined how NRG-HSPG interactions affect NRG-erbB receptor binding, erbB receptor auto-phosphorylation and downstream activation of AChR genes and newly-synthesized proteins in primary chick myotube cultures. Using recombinant NRG β1 isoforms with and without the HBD, it is demonstrated herein that the N-HBD potentiated the EGF-like domain's action on receptor phosphorylation by interacting with endogenous HSPGs. Through these HSPG interactions, the N-HBD induces sustained NRG-erbB receptor phosphorylation for over 8 hrs that is required, for example, to turn on AChR mRNA and protein expression. These results provide a molecular rationale for the high concentration of NRG in the ECM of neuromuscular synapses.

The N-HBD contains two Cys residues separated by 55 amino acids with a Trp located 13 residues from the first Cys. This is characteristic of the Ig C2 subfamily of Ig gene superfamily. For example the native human N-HBD sequence had only 32% identity with a more "conventional" Ig C2 Ig domain found on CD4. The N-HBD, homologue or functional derivative of the present invention preferably has the above sequence characteristic and less than about 40% identity with an Ig C2 domain of an Ig H or L chain from the same animal species.

The present invention is directed in particular to a novel hybrid or fusion polypeptide that includes at least two domains or peptidic structures: (1) a first "targeting" polypeptide domain whose role is to target the fusion polypeptide, and (2) a fusion partner referred to herein as a "targeted" polypeptide or "$P_{trg}$." The targeting domain is preferably an animal N-HBD, more preferably a mammalian N-HBD, most preferably a human N-HBD. Some of the Examples below show results obtained using a chicken N-HBD, which has features in common with human N-HBD, including sequence identity or similarity.

In one embodiment, DNA encoding the amino acid sequence corresponding to the N-HBD, containing or a biologically active fragment thereof is joined to DNA encoding a $P_{trg}$, for example, by PCR, to form a construct that is expressed as an N-HBD/$P_{trg}$ fusion protein.

The present invention is thus directed to an isolated nucleic acid molecule of no more than about 100 nucleotides that encodes an animal N-HBD polypeptide or a functional derivative of the polypeptide, which polypeptide or functional derivative is characterized in that it (a) is a member of the C2 subfamily of the immunoglobulin superfamily but has less than about 40% sequence identity to a C2 domain of an Ig H or L chain from the same animal species; and (b) binds to heparin or to a heparan sulfate proteoglycan with a $K_d$ of about $10^{-5}$M or lower when measured in a conventional heparin-binding or heparan-sulfate binding assay.

In the above nucleic acid molecule, the N-HBD polypeptide preferably comprises an amino acid sequence selected from the group consisting of:

(a) GSKLVLRCET SSEYSSLRFK WFKNGNELNR KNKPQNIKIQ KKPGKSELRI NKASLADSGE YMCKVISKLG (SEQ ID NO:1) from human NRG;

(b) GSKLVLRCET SSEYSSLRFK WFKNGNELDN KNKPENIKIQ KKPGKSELRI NKASLADSGE YMCKVISKLG (SEQ ID NO: 2) from rat NRG;

(c) GQKLVLRCET TSEYPALRKW LKNGKETTKK NRPENVKIPK KQKKYSELHI YRATLADAGE YACRVSSKLG SEQ ID NO:3 from avian NRG; and (d) a functional derivative or homologue of (a), (b) or (c).

The above nucleic acid molecule may comprises a nucleotide sequence selected from the group consisting of SEQ ID NO:4, SEQ ID NO:5 or (SEQ ID NO:6).

In another embodiment, the invention is an isolated nucleic acid molecule of no more than about 100 nucleotides that hybridizes with any of the above nucleic acid molecules under stringent hybridization conditions.

The present invention is directed to a hybrid nucleic acid molecule encoding a N-HBD fusion polypeptide, which molecule comprises:
(a) as a first nucleic acid sequence, any of the above nucleic acid molecules;
(b) optionally, fused in frame with the first nucleic acid sequence, a linker nucleic acid sequence encoding a linker peptide; and
(c) a second nucleic acid sequence that (i) is linked in frame to the first nucleic acid sequence or to the linker nucleic acid sequence and (ii) encodes a second polypeptide $P_{trg}$.

Preferably, in the above hybrid nucleic acid, the second polypeptide $P_{trg}$ is:
(a) a soluble form of a cell surface receptor that is capable, as part of the fusion polypeptide, of binding a ligand for the receptor, thereby acting as an antagonist for ligand activation of the receptor; or
(b) a ligand for a cell surface receptor that is capable, as part of the fusion polypeptide, of binding to the receptor and thereby acting as either an agonist or antagonist at the receptor, depending in part on affinity and concentration.

The receptor is preferably a tyrosine kinase receptor, a G-protein-coupled receptor or an antibody, most preferably a tyrosine kinase receptor. A preferred receptor is an EGF receptor. The ligand may be a cytokine or growth factor, preferably an epidermal growth factor, a fibroblast growth factor, a neurotrophic factor, a vascular endothelial growth factor, a transforming growth factor, a netrin or an ephrin.

Also provided is an expression vector comprising the above nucleic acid molecule operatively linked to (a) a promoter and (b) optionally, additional regulatory sequences that regulate expression of the nucleic acid in a eukaryotic cell, which vector can be expressed in a cell after delivery to the cell in vitro or in vivo. Preferred vectors are plasmids or viral vectors.

A related embodiment is a vector composition, comprising
(a) a first recombinant expression vector having incorporated in its nucleic acid one or more nucleotide sequences encoding a N-HBD polypeptide or a biologically active fragment, homologue or other functional derivative thereof; and
(b) a second recombinant expression vector having incorporated in its nucleic acid a nucleotide sequence encoding a polypeptide $P_{trg}$, which is (i) a soluble form of a cell surface receptor that is capable, as part of the fusion polypeptide, of binding a ligand for the receptor, thereby acting as an antagonist for ligand activation of the receptor; or (ii) a ligand for a cell surface receptor that is capable, as part of the fusion polypeptide, of binding to the receptor and thereby acting as either an agonist or antagonist at the receptor.

wherein the expression vectors are able to co-infect or co-transfect a host cell resulting in co-expression of $P_{trg}$ and the N-HBD polypeptide, fragment, homologue or derivative.

In the vector composition, the first vector preferably comprises SEQ ID NO:4, SEQ ID NO:5 or (SEQ ID NO:6).

The present invention provides a cell transformed or transfected with any of the above nucleic acid molecules or vectors, preferably a mammalian cell, most preferably a human cell. One embodiment is an isolated mammalian cell transfected with an exogenous nucleic acid molecule encoding a mammalian N-HBD polypeptide or a biologically active fragment, homologue or other functional derivative thereof, such that the polypeptide, fragment, homologue or derivative is expressed by the cell, which polypeptide or functional derivative
(a) is a member of the C2 subfamily of the immunoglobulin superfamily but has less than about 40% sequence identity to a C2 domain of an Ig H or L chain from the same animal species; and
(b) binds to heparin or to heparan sulfate proteoglycans with a $K_d$ of about $10^{-5}$M or lower when measured in a conventional heparin-binding or heparan-sulfate binding assay.

In the above cell, the exogenous nucleic acid molecule preferably comprises SEQ ID NO:4, SEQ ID NO:5 or SEQ ID NO:6, or a homologue, fragment or functional derivative thereof.

This invention is also directed to a fusion polypeptide comprising
(a) a first targeting polypeptide that binds heparan sulfate when the fusion polypeptide is permitted to contact cells or tissues, thereby localizing the fusion polypeptide to the heparan-sulfate rich cell or tissue surface; wherein the fusion protein binds to heparin or to a heparan sulfate proteoglycan with a $K_d$ of $10^{-5}$M or lower when measured in a conventional heparin-binding or heparan-sulfate binding assay; and
(b) a second targeted polypeptide $P_{trg}$ that is to be targeted and localized to the heparan sulfate-rich cell or tissue surface;

wherein the fusion polypeptide, through the action of the $P_{trg}$, has enhanced biological activity in stimulating or blocking a target receptor compared to native $P_{trg}$ or $P_{trg}$ not fused to the targeting polypeptide.

In the above fusion polypeptide, the first targeting polypeptide preferably comprises all or a part of a N-HBD or a homologue or functional derivative thereof which (i) is fused directly to the second targeted polypeptide or, (ii) optionally, is fused to a linker peptide sequence that is fused to the second targeted polypeptide. The targeting polypeptide sequence is preferably encoded by the a nucleic acid molecule as described above, or by a fragment, homologue or equivalent of the nucleic acid molecule.

The above fusion polypeptide or biologically active fragment, homologue or other functional derivative of the polypeptide is preferably produced by recombinant expression of the above expression vector or vector composition.

In the above fusion polypeptide, the targeting polypeptide preferably has the amino acid sequence SEQ ID NO:1, SEQ ID NO:2 or SEQ ID NO:3, or a heparin binding functional derivative or homologue thereof. A preferred functional derivative is a fragment having the sequence KWFKNGNEL-NRKNKPQNIKIQKKPGK (SEQ ID NO: 7), KWFKNG-NELNRKNKPENIKIQKKPGK (SEQ ID NO:8) or KWLKNGKEITKKNRPENVKIPKKQKK (SEQ ID NO:9).

In another embodiment the functional derivative is a polypeptide having the sequence K-x-x-K-x-x-x-x-x-R-K-x-K-x-x-x-x-K-x-x-K-K-x-x-K (SEQ ID NO:10), wherein x is any amino acid, or a fragment thereof having at least four, preferably at least six Lys or Arg residues. The fragment may have any consensus heparin binding sequence, for example Z-x-Z-Z, wherein Z is a basic amino acid.

Preferably, the above fusion polypeptide binds to heparan sulfate with an affinity characterized by a $K_d$ of less than about $10^{-5}$M and has enhanced biological activity in stimulating or blocking a target receptor compared to native $P_{trg}$ or $P_{trg}$ not fused to the targeting polypeptide.

In the above fusion polypeptides, the linker, if present, may be one cleavable by a protease, such as VPRGSD (SEQ ID NO:11) or DDKDWH (SEQ ID NO:12).

The fusion polypeptide may be a linear multimer of two or more repeats of monomers of the first targeting polypeptide linked end to end (i) directly or (ii) with a linker sequence present between the monomer repeats. One example, comprises a tandemly linked dimer or trimer of the first targeting polypeptide fused to the second targeted polypeptide. The second "targeted" polypeptide $P_{trg}$ is preferably (a) a soluble form of a cell surface receptor that is capable, as part of the fusion polypeptide, of binding a ligand for the receptor, thereby acting as an antagonist for ligand activation of the receptor;

(b) a ligand for a cell surface receptor that is capable, as part of the fusion polypeptide, of binding to the receptor and thereby acting as either an agonist or antagonist at the receptor.

As indicated above, the receptor may be a tyrosine kinase receptor, a G-protein coupled receptor or an antibody, preferably an EGF receptor. The ligand is a cytokine or growth factor, preferably an epidermal growth factor, a fibroblast growth factor, a neurotrophic factor, a vascular endothelial growth factor, a transforming growth factor, a netrin or an ephrin. A preferred neurotrophic factor is brain derived neurotrophic factor, glial derived neurotrophic factor, neurotrophin 3, neurotrophin 4, or nerve growth factor.

The present invention also provides a pharmaceutical composition useful for delivering a targeted polypeptide to a cell or tissue surface and enhancing the biological activity of the targeted polypeptide, comprising: (a) the fusion polypeptide described above; and (b) a pharmaceutically acceptable excipient or carrier.

Also provided is a mammalian, preferably human, cell that expresses on its surface or secretes the above fusion polypeptide.

Another pharmaceutical composition that is useful for delivering a targeted polypeptide that is in a form expressed on the surface of, or secreted by, a recombinant cell, comprises (a) a cell as described above and (b) a pharmaceutically acceptable excipient or carrier.

This invention is further directed to a method for localizing a targeted polypeptide to a cell or tissue surface rich in heparan sulfate, and thereby enhancing its biological activity at the surface, comprising providing to the surface the fusion polypeptide of any of claims 28-46 whereby the $P_{trg}$ of the fusion polypeptide is localized to the surface, such that the biological activity of the $P_{trg}$ is increased compared to the activity of native $P_{trg}$ or $P_{trg}$ not fused to the targeting polypeptide. The providing is preferably in vivo.

Also included is a method for treating a disease or condition in a subject treatable by the action of the $P_{trg}$, comprising administering to the subject an effective amount of the above pharmaceutical composition, whereby the biological activity of the $P_{trg}$ of the fusion polypeptide is increased compared to the activity of native $P_{trg}$ or $P_{trg}$ not fused to the targeting polypeptide, thereby treating the disease or condition.

The method for treating a disease or condition in a subject treatable by the action of the $P_{trg}$, may comprise administering to the subject an effective amount of the above cellular pharmaceutical composition, whereby cells bearing or secreting the $P_{trg}$ are made available to the cell or tissue surface, and wherein, the biological activity of the $P_{trg}$ is increased compared to the activity of native $P_{trg}$ or $P_{trg}$ not fused to the targeting polypeptide, thereby treating the disease or condition.

In the above method, the disease or condition may be a tumor or cancer.

In another embodiment, the disease or condition is a neurological disorder, for example, a neurodegenerative disease, multiple sclerosis, stroke, epilepsy or traumatic brain, spinal cord or peripheral nerve injury. Neurodegenerative diseases treatable by this method include Alzheimer's disease, Parkinson's disease and amyotrophic lateral sclerosis.

BRIEF DESCRIPTION OF THE DRAWINGS

FIG. 3A shows the results of a competitive binding assay of $^{125}$I-NRG. $^{125}$I-IG-EGF NRG was applied to chick myotube cultures for 2 hrs on ice without or with cold ligand IG-EGF (NRG) or soluble heparin. Total cpm bound was measured for untreated myotubes and myotubes pre-treated for 90 min. with heparitinase (to remove endogenous heparan sulfate) or chondroitinase (to remove chondroitin sulfate). Non-specific binding was about 50%. Both cold NRG and heparitinase reduced binding by a similar proportion (25%). Heparin blocked binding by the sum of both of these, or 50%. Treatment with chondroitinase had no effect on NRG binding. FIG. 2B shows that potentiation of receptor phosphorylation by the IG-EGF construct was reduced to the level as that induced by the EGF construct after treatment with heparitinase. Confluent chick myotube cultures were pretreated with or without heparitinase (0.04 U/ml) in 0.1% BSA/MEM for 2 hrs. The recombinant NRG forms were then applied to these cultures for 45 min after which p185 phosphorylation activity was examined by western blot. This gel was resolved further than previous gels and thus separated p185 into two bands. Treatment with heparitinase had no effect on the activity of the EGF-like domain alone, but reduced phosphorylation induced by IG-EGF to the same level as the EGF-like domain.

Quantitation shown in histogram form, was normalized to 100% for the maximal response(IG-EGF.

Figure 4:
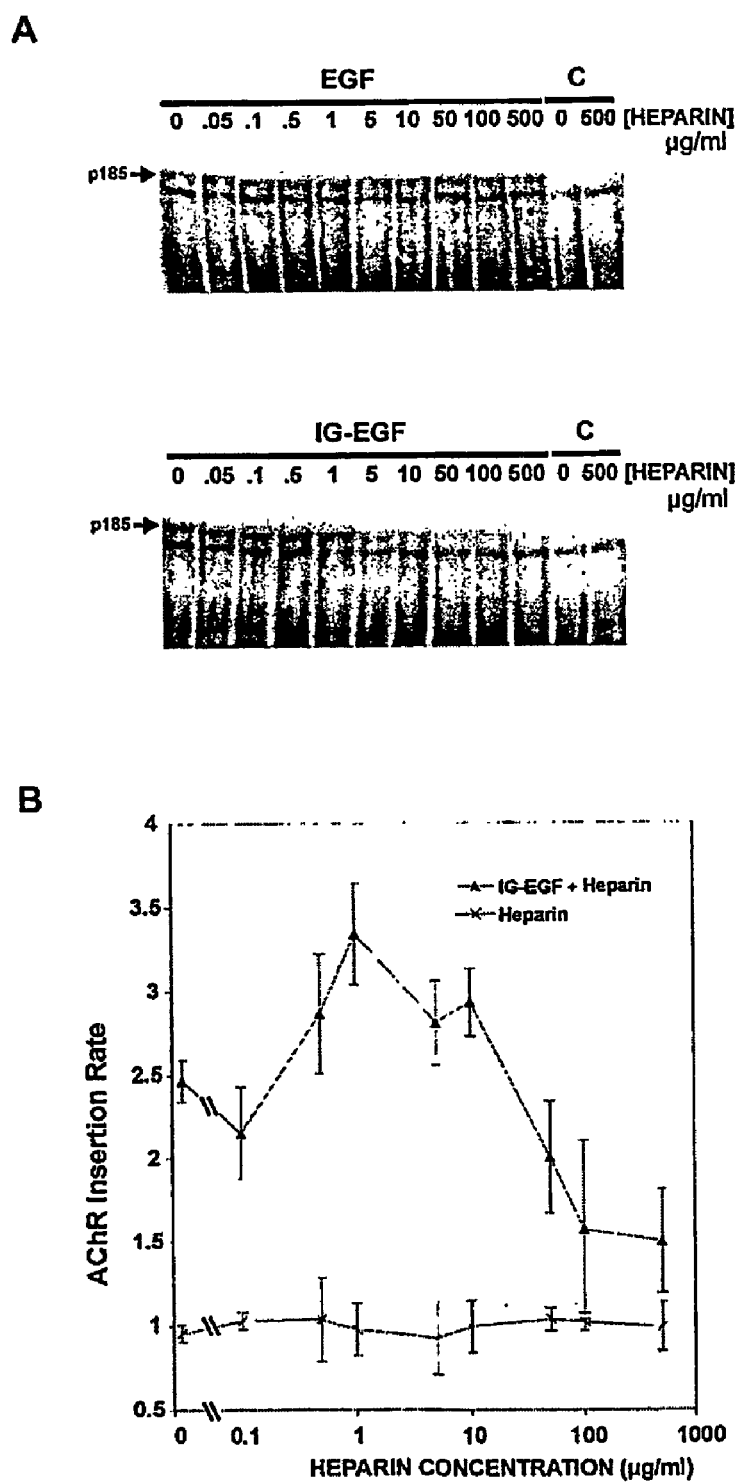

FIGS. 4A and 4B are a series of western blots and a graph showing the effect of heparin on receptor phosphorylation and AChR protein expression. Results in FIG. 4A show that treatment with heparin blocked NRG-induced erbB receptor phosphorylation (p185) only when NRG constructs included both IG- and EGF-like domains. Recombinant NRG forms (1 nM) were mixed with increasing concentrations of heparin and added to confluent chick myotube cultures for 45 min. p185 phosphorylation was analyzed by western blot. Heparin had no effect on receptor phosphorylation by the EGF-like domain alone, but blocked p185 phosphorylation with the IG-EGF construct when heparin concentrations were greater than 1 µg/ml. In the study resulting in FIG. 4B, chick myotube cultures were treated with a combination of 500 pM NRG (IG-EGF) and increasing concentrations of heparin for 18 hrs, and the insertion rate of new AChRs into the membrane was measured. This was achieved by blocking AChR binding sites with cold α-bungarotoxin, allowing newly synthesized AChRs to appear in the plasma membrane, and then measuring these new AChRs by binding of 125I α-bungarotoxin. Heparin had a biphasic effect on the AChR insertion rate—stimulatory at low concentrations and inhibitory at high concentrations. Heparin alone had no effect. Error bars show standard deviation of the mean.

Figure 1:
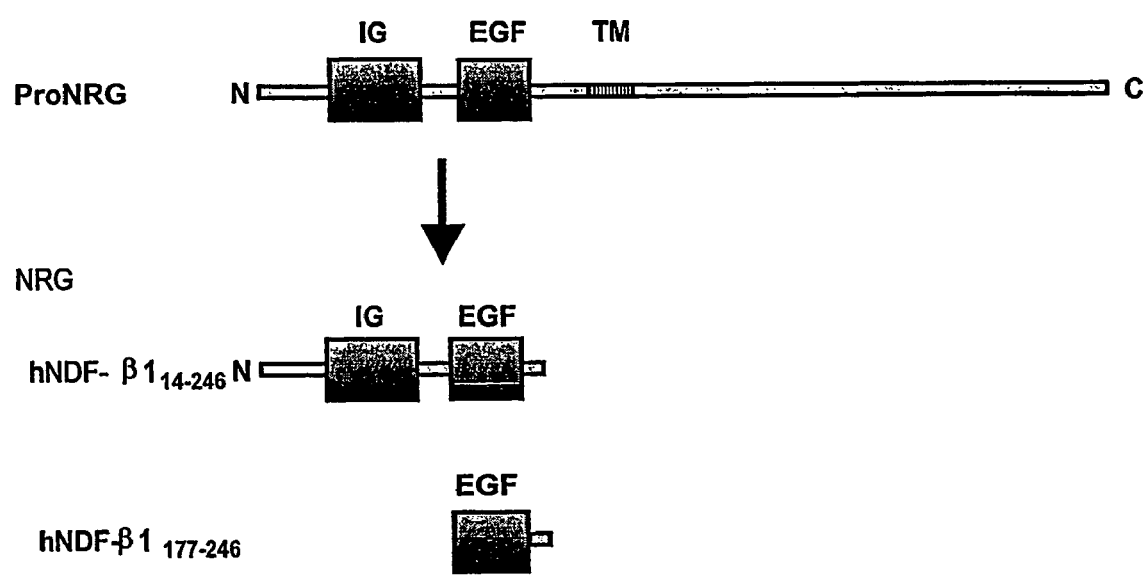
FIG. 1 shows NRG domain structure and constructs used. Type I β1 NRGs are initially synthesized as a transmembrane precursors called proNRG with a C-terminal cytoplasmic domain and a single membrane spanning domain TM. It is cleaved just outside the transmembrane domain and the soluble polypeptide containing the IG and the EGF domains is released. The isolated EGF-like domain construct used here corresponds to amino acid 177-246, and the IG-EGF domain construct corresponds to amino acid 14-246 of the human β1 form.
Figure 5:
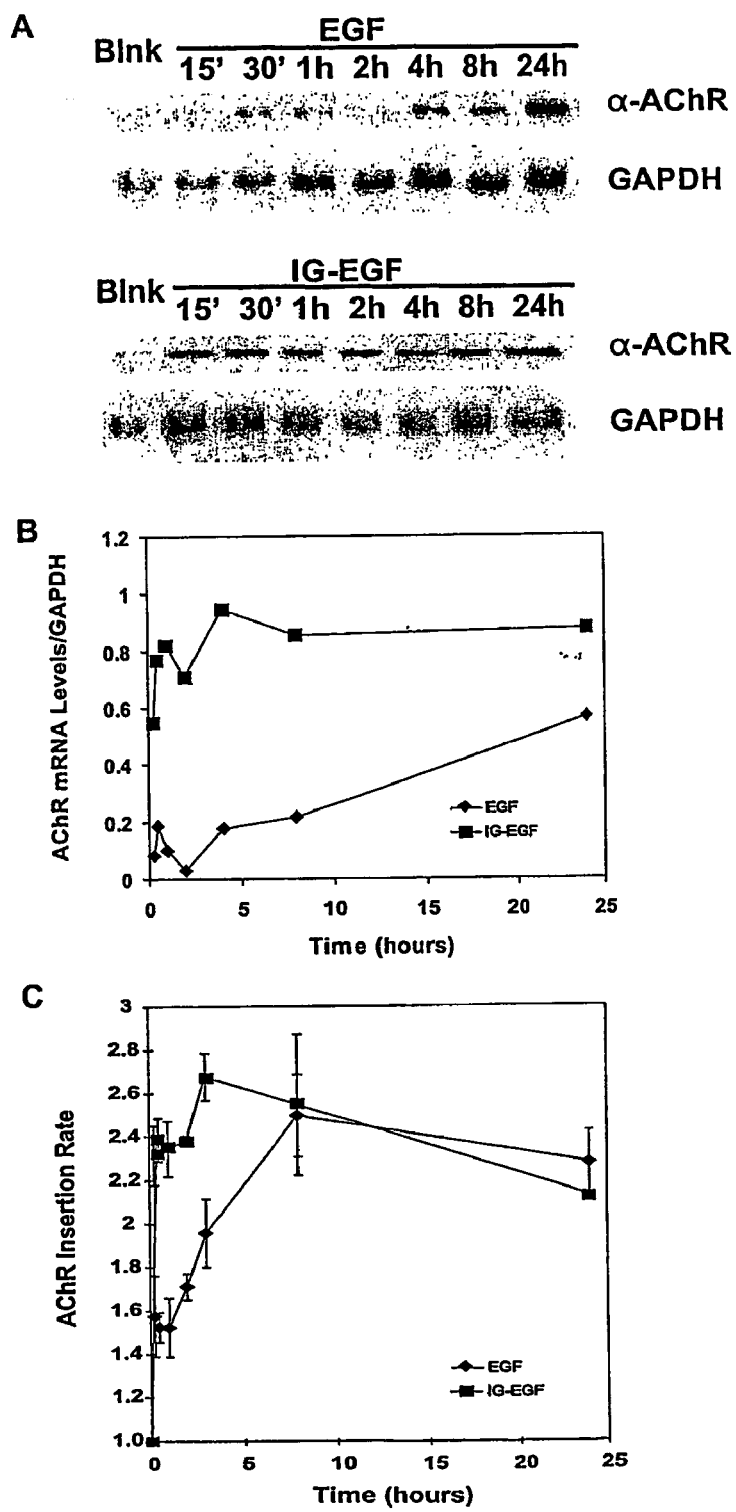

FIGS. 5A, 5B and 5C is a series of blots and graphs showing that the IG domain of NRG enhances AChR mRNA and protein expression by providing a sustained source of ligand. In the experiment of FIG. 5A, 1 nM of EGF or IG-EGF constructs were applied to chick myotube cultures for the indicated times and then washed away at the indicated times. These cultures were allowed to complete a 24-hr incubation period before AChR mRNA level and protein insertion rate were measured. RNA was extracted and a northern blot using a probe specific to the AChR α subunit was performed. The membrane was then re-probed with the housekeeping gene GAPDH to normalize the data. FIG. 5B shows quantitative measurements of the AChR/GAPDH ratio, and demonstrate that maximal activation of AChR mRNA expression by IG-EGF was achieved in 15 min, compared to the EGF-like domain, which was not maximal even after 24 hrs. FIG. 4C shows AChR protein insertion rate, measured at the same times, points. Over 8 hrs of exposure to the EGF-like domain was required to evoke a response of the magnitude evoked in 15 min by the IG-EGF construct. This result suggests that the IG-like domain keeps NRG at a sufficiently high concentration for a sufficient duration to increase AChR mRNA and protein.

Figure 3:
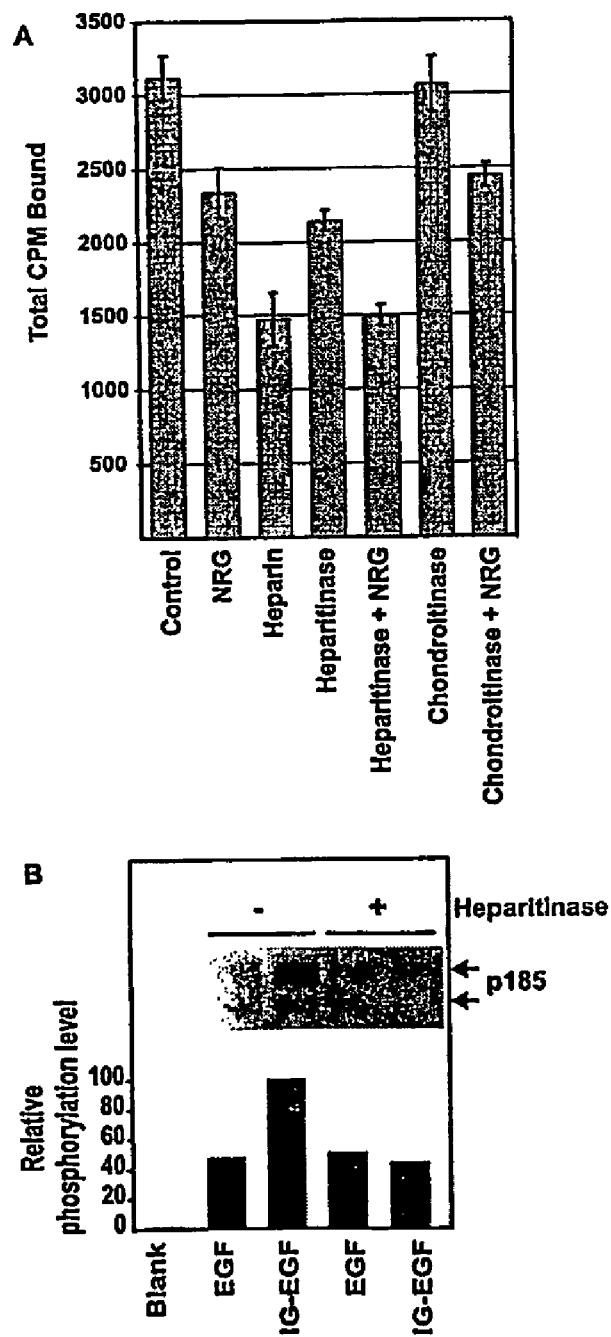
FIGS. 3A and 3B are a set of graphs showing enhanced p185 phosphorylation is due to NRG-HSPG interactions.
Figure 6:
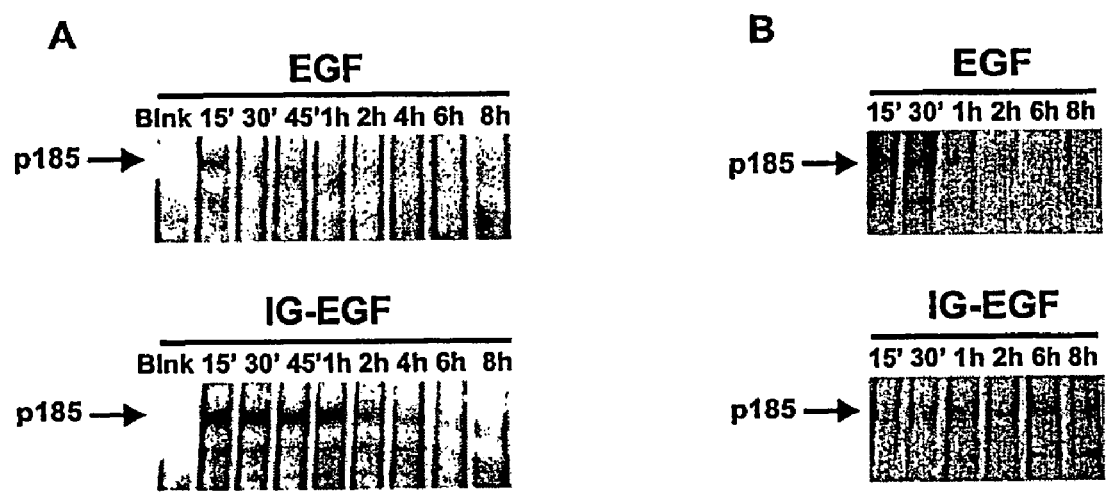

FIGS. 6A and 6B is a set of blots showing that the IG-like domain of NRG keeps erbB receptors in a phosphorylated state for 24 hrs. FIG. 6A shows a time course of receptor phosphorylation. EGF or IG-EGF, constructs were applied to chick myotube cultures for increasing periods of time after which p185 receptor phosphorylation (arrows) was measured by western blot. While phosphorylation was greater initially, particularly with the IG-EGF construct, both constructs kept the multiple erbB receptors in a phosphorylated state (resolved as in FIG. 3B) for 24 hrs, compared to the level of receptor phosphorylation seen without NRG (Blnk). FIG. 6B shows that ErbB receptor phosphorylation wanes within one hr after the EGF construct is washed away. Chick myotube cultures were treated with 1 nM recombinant NRG (EGF of IG-EGF) for 45 min. Cultures were washed twice with medium. p185 phosphorylation (arrows) was subsequently measured by western blot at the indicated time points after the wash. Receptor phosphorylation induced by the EGF-like domain alone decayed within 1 hr of the wash. In contrast, the IG-EGF construct maintained receptor phosphorylation even 8 hrs after the wash, suggesting that the construct was not washed away.

Figure 7:
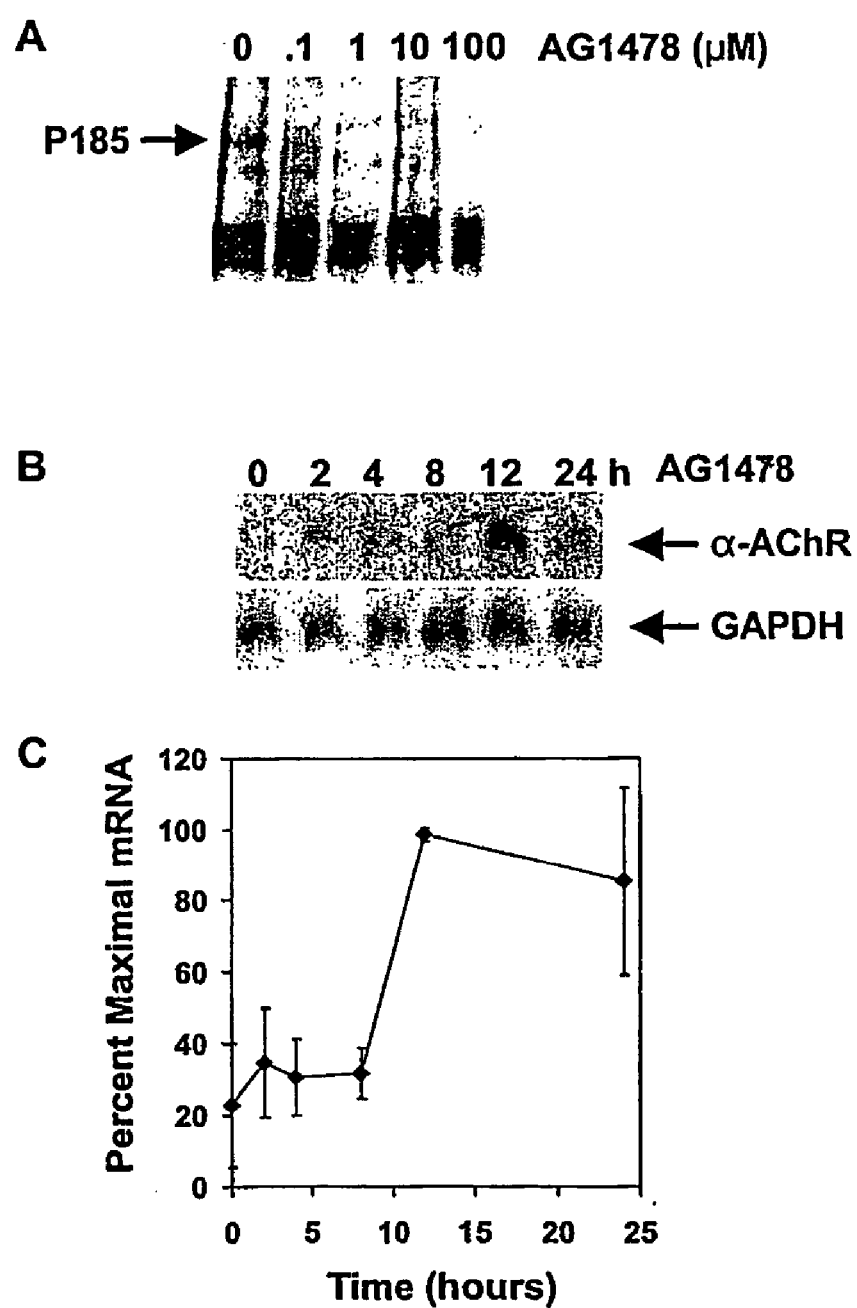

FIG. 7 is a series of blots and a graph showing that the induction of AChR—subunit mRNA required sustained erbB receptor phosphorylation for at least 8 hrs. In order to determine the concentration of a specific tyrosine kinase antagonist (AG1478) that blocks erbB receptor phosphorylation, chick myotube cultures were exposed to 1 nM of the EGF construct mixed with increasing concentrations of AG1478 for 45 min after which p185 receptor phosphorylation was measured by western blot (FIG. 7A). $\geq 1$ µM AG1478 was sufficient to completely block erbB tyrosine kinase activity. Therefore 10 µM AG1478 was the concentration selected for further use. Primary myotubes were treated with 1 nM of the EGF construct for a total time period of 24 hrs before AChR α-subunit mRNA levels were measured by northern blot (FIG. 7B). At different intervals after NRG treatment, AG1478 (10 µM) was added to the cultures to block erbB receptor phosphorylation. The results showed that 12 hrs of receptor phosphorylation was needed to increase AChR mRNA levels. FIG. 7C shows quantitative measurements of the AChR/GAPDH ratio from three separate experiments, normalized to 100% for the maximal activation of AChR mRNA and expressed as mean ±1 standard deviation. 12 hrs or more of sustained receptor phosphorylation was necessary to increase AChR mRNA levels.

Figure 8A:
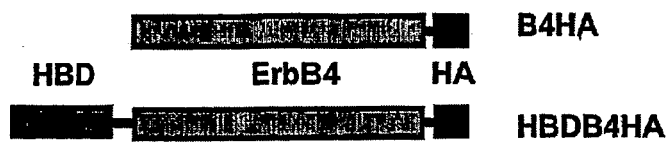
Figure 8B:
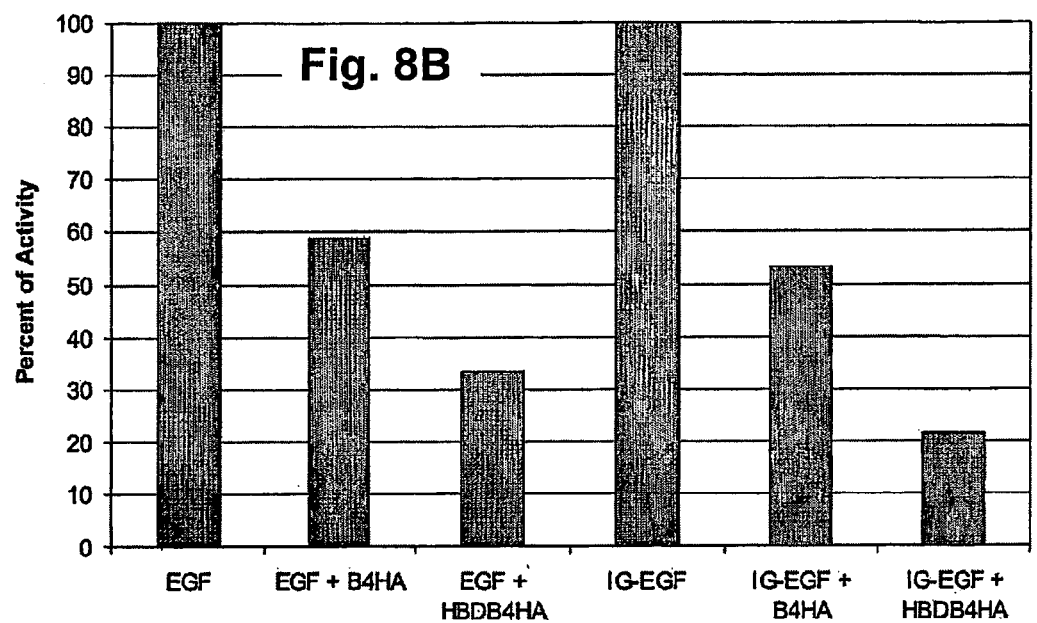
Figure 8C:

FIG. 8A-8C show two fusion constructs of N-HBD ("HBV") fused to ErbB4 (tyrosine kinase receptor) (ErbB4) and the hemagglutinin epitope tag (HA). These were tested as antagonists which antagonize the tyrosine phosphorylation of cellular ErbB4 on L6 muscle cells induced by the NRG EGF domain or a dual domain NRG agonist that comprises EGF and the IG-like domain (IG-EGF). The graph of FIG. 8B shows the relative tyrosine phosphorylation responses in Western blots (detected by an anti-P-Tyr antibody). FIG. 8C shows an actual gel pattern (SDS-PAGE, 5%) for the agonists alone, or combinations of agonists and antagonists.

DESCRIPTION OF THE PREFERRED EMBODIMENTS

Neuregulins (NRGs) bind to and activate members of the EGF receptor family of tyrosine kinases, thereby initiating a signaling cascade. When the target is the postsynaptic membrane of neuromuscular synapses, one consequence of this activation is the induction of AChR synthesis. In addition to an EGF-like domain, responsible for, and sufficient for receptor binding and tyrosine auto-phosphorylation, many spliced forms of NRGs also have an IG-like domain (=N-HBD) that binds HSPGs and maintains a high concentration of NRG at the synapse.

The present inventor has discovered that the N-HBD functions to keep the EGF-like domain at sufficiently high concentrations for a sufficiently long interval to permit induction of AChR gene expression in primary chick myotubes as a model system. Using recombinant NRGs with and without the N-HBD, it was discovered that N-HBD binding to endogenous HSPGs produces a 4-fold increase in receptor phosphorylation, an effect which was blocked by soluble heparin or by pre-treatment of the muscle cells with the enzyme heparitinase. At least 12-24 hrs of NRG exposure was found to be required to turn on substantial AChR gene expression and that it was important that erbB receptors were kept phosphorylated during this time. The need for sustained erbB receptor activation explains why NRGs are so highly concentrated in the ECM of synapses.

Based on these observations, the present inventor conceived of a broader utility for the N-HBD of NRG, to target any protein or polypeptide to which the domain is fused to a site rich in any binding partner for the domain, whether currently known or later discovered. Primarily such sites are known to be cell surfaces and ECM where HSPGs are expressed.

General References

Unless otherwise indicated, the practice of many aspects of the present invention employs conventional techniques of molecular biology, recombinant DNA technology and immunology, which are within the skill of the art. Such techniques are described in more detail in the scientific literature, for example, Sambrook, J. et al., *Molecular Cloning: A Laboratory Manual*, 2$^{nd}$ Ed., Cold Spring Harbor Press, Cold Spring Harbor, N.Y., 1989, Ausubel, F. M. et al. *Current Protocols in Molecular Biology*, Wiley-Interscience, New York, current volume; Albers, B. et al., *Molecular Biology of the Cell*, 2$^{nd}$ Ed., Garland Publishing, Inc., New York, N.Y. (1989); Lewin, B M, *Genes IV*, Oxford University Press, Oxford, (1990); Watson, J. D. et al., *Recombinant DNA*, Second Edition, Scientific American Books, New York, 1992; Darnell, J E et al., *Molecular Cell Biology*, Scientific American Books, Inc., New York, N.Y. (1986); Old, R. W. et al., *Principles of Gene Manipulation: An Introduction to Genetic Engineering*, 2$^{nd}$ Ed., University of California Press, Berkeley, Calif. (1981); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *Methods in Enzymology: Guide to Molecular Cloning Techniques*, (Berger and Kimmel, eds., 1987); Hartlow, E. et al., *Antibodies: A Laboratory Manual*, Cold Spring Harbor Laboratory Press, Cold Spring Harbor, N.Y., 1988), Coligan, J E et al., eds., *Current Protocols in Immunology*, Wiley-Interscience, New York 1991. Protein structure and function is discussed in Schulz, G E et al., *Principles of Protein Structure*, Springer-Verlag, New York, 1978, and Creighton, T E, *Proteins: Structure and Molecular Properties*, W. H. Freeman & Co., San Francisco, 1983.

In one embodiment, DNA encoding the amino acid sequence corresponding to the N-HBD, from human or other mammals is used. Preferred DNA sequences are:

(SEQ ID NO:4)
ggt tcc aaa cta gtc ctt cgg tgt gaa acc agt tct gaa tac tcc tct ctc aga ttc aag tgg ttc aag aat ggg aat gaa ttg aat cga aaa aac aaa cca caa aat atc aag ata caa aaa aag cca ggg aag tca gaa ctt cgc att aac aaa gca tca ctg gct gat tct gga gag tat atg tgc aaa gtg atc agc aaa tta gga;

(SEQ ID NO:5)
ggc tcc aag cta gtg ctc cgg tgc gaa acc agc tcc gag tac tcc tca ctc aga ttc aaa tgg ttc aag aat ggg aac gag ctg aac cgc aaa aat aaa cca gaa aac atc aag ata cag aac aag cca ggg aag tca gag ctt cga att aac aaa gca tcc ctg gct gac tct gga gag tat atg tgc aaa gtg atc agc aag tta gga;
and (SEQ ID NO:6)
ggt cag aag cta gtg cta agg tgt gaa acc act tca gag tac cct gcg ctc aga ttc aaa tgg tta aag aac ggg aag gaa ata acg aaa aaa aac aga ccc gaa aat gtc aag atc ccc aaa aag caa aag aaa tac tct gag ctt cat att tat aga gcc acg ttg gct gac gct ggg gaa tac gca tgc aga gtg agc agc aaa cta ggg.

Preferably, this is joined to DNA encoding the amino acid sequences of a polypeptide or peptide to be targeted ("P$_{trg}$") (to cell surfaces or ECM) using PCR, to form a construct that is expressed as N-HBD-P$_{trg}$ fusion protein. The techniques for assembling and expressing DNA encoding the N-HBD fusion proteins such as synthesis of oligonucleotides, PCR, transforming cells, constructing vectors, expression systems, and the like are well-established in the art. Those of ordinary skill are familiar with the standard resource materials, specific conditions and procedures.

Expression Vectors and Host Cells

This invention includes an expression vector comprising a nucleic acid sequence encoding an IG-domain fusion polypeptide operably linked to at least one regulatory sequence. "Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

Those skilled in the art appreciate that the particular design of an expression vector of this invention depends on considerations such as the host cell to be transfected and/or the type of protein to be expressed.

The present expression vectors comprise the full range of nucleic acid molecules encoding the various embodiments of N-HBD when included in a fusion protein: full length domain, and its functional derivatives (defined herein) including polypeptide fragments, variants, etc. Thus, in one embodiment, the expression vector comprises a nucleic acid encoding at least a portion of the N-HBD alone or fused to another polypeptide.

Such expression vectors are used to transfect host cells for expression of the DNA and production of the encoded proteins which include fusion proteins or peptides. It will be understood that a genetically modified cell expressing the N-HBD polypeptide may transiently express the exogenous DNA for a time sufficient for the cell to be useful for its stated purpose. Thus, if the cell is to serve as a production source or delivery vehicle for the fusion polypeptide in vivo, the length of time that expression is required, or that the cell remain alive, is the time necessary for the cell to exert its production/delivery, function. For example, expression of an N-HBD fusion polypeptide may be for as little as 6 hrs, preferably 24 hrs, more preferably for at least 2-4 days. Of course, expression may also be stable (i.e., for the life of the cell). Appropriate expression vectors and regulatory elements (e.g., inducible or constitutive promoters) discussed below are selected in accordance with the desired or required stability of expression.

The present in invention provides methods for producing the N-HBD polypeptide and derivatives. For example, a host cell transfected with a nucleic acid vector that encodes a fusion protein comprising at least a portion of the N-HBD polypeptide is cultured under appropriate conditions to allow expression of the fusion polypeptide.

Host cells may also be transfected with one or more expression vectors that singly or in combination comprise DNA encoding at least a portion of the N-HBD protein and DNA encoding at least a portion of a second protein (the $P_{trg}$ so that the host cells produce the fusion polypeptides that include both the portions.

When the recombinant expression vector comprises DNA encoding a portion of N-HBD and DNA encoding a $P_{trg}$, the resulting fusion protein may have altered solubility, binding affinity and/or valency. A N-HBD fusion protein is preferably secreted by transfected host cells in cultures and is therefor isolated from the culture medium. Alternatively, if protein is retained in the cytoplasm, the cells are harvested and lysed and the protein isolated from this lysate.

A culture typically includes host cells, appropriate growth media and other byproducts. Suitable culture media are well known in the art. N-HBD protein can be isolated from medium or cell lysates using conventional techniques for purifying proteins and peptides, including ammonium sulfate precipitation, fractionation column chromatography (e.g. ion exchange, gel filtration, affinity chromatography, etc.) and/or electrophoresis (see generally, "Enzyme Purification and Related Techniques", *Methods in Enzymology,* 22: 233-577 (1971)). Once purified, partially or to homogeneity, the recombinant N-HBD fusion polypeptides of the invention can be utilized in pharmaceutical compositions as described in more detail herein.

Prokaryotic or eukaryotic host cells transformed or transfected to express N-HBD or functional derivative thereof, preferably fusion polypeptides, are within the scope of the invention. For example, N-HBD may be expressed in bacterial cells such as *E. coli,* insect cells (baculovirus), yeast, or mammalian cells such as Chinese hamster ovary cells (CHO) or human cells. Other suitable host cells may be found in Goeddel, (1990) supra or are otherwise known to those skilled in the art.

Expression in eukaryotic cells leads to partial or complete glycosylation and/or formation of relevant inter- or intra-chain disulfide bonds of the recombinant protein.

Examples of vectors for expression in yeast *S. cerevisiae* include pYepSec1 (Baldari et al., (1987) *EMBO J.* 6:229-234), pMFa (Kurjan et al. (1982) *Cell* 30:933-943), pJRY88 (Schultz et al., (1987) *Gene* 54:113-123), and pYES2 (invitrogen Corporation, San Diego, Calif.). Baculovirus vectors available for expression of proteins in cultured insect cells (SF 9 cells) include the pAc series (Smith et al., (1983) *Mol. Cell Biol.* 3: 2156-2165,) and the pVL series (Lucklow, V. A., and Summers, M. D., (1989) *Virology* 170: 31-39). Generally, COS cells (Gluzman, Y., (1981) *Cell* 23: 175-182) are used in conjunction with such vectors as pCDM 8 (Aruffo A. and Seed, B., supra, for transient amplification/expression in mammalian cells, while CHO (dhfr-negative CHO) cells are used with vectors such as pMT2PC (Kaufman et al. (1987), *EMBO J.* 6: 187-195) for stable amplification/expression in mammalian cells. The NS0 myeloma cell line (a glutamine synthetase expression system.) is available from Celltech Ltd.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase. These are discussed more below.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Inducible non-fusion expression vectors include pTrc (Amann et al., (1988) *Gene* 69: 301-315) and pET 11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET 11d relies on transcription from the T7 gn10-lacO fusion promoter mediated by coexpressed viral RNA polymerase (T7gn1). Th is viral polymerase is supplied by host strains BL21(DE3) or HMS174(DE3) from a resident λ prophage harboring a T7gn1 under the transcriptional control of the lacUV 5 promoter.

One embodiment of this invention is a transfected cell which expresses a novel N-HBD fusion polypeptide de novo. In the case of a cell already expressing a N-HBD, the present invention provides a transfected cell expressing increased amounts of the N-HBD polypeptide or functional derivative (defined below). The nucleic acid constructs of this invention can be expressed in cells or tumors for purposes of paracrine release and binding to the expressing cells themselves or to other nearby cells which are being targeted. For example, a tumor cell such as a sarcoma, melanoma, leukemia, lymphoma, carcinoma or neuroblastoma is transfected with an expression vector directing the expression of N-HBD or fusion polypeptide on the tumor cell surface. Such transfected tumor cells can be directed to sites rich in HSPGs. Moreover, cells co-expressing on their surface an N-HBD and an immunostimulatory cytokine (e.g., IL-2, IL-4, GM-CSF, and the like) can potentiate the action of the cytokine at a tumor site.

Tumor cells are known to express differential amounts of HSPGs that correlate with their metastatic potential. The balance between HSPG expression and enzymes that degrade HSPGs can drastically affect their growth and metastasis. For example, pre-treatment of MCF-7 cells with heparanase blocks FGF-induced cell growth, whereas chlorate treatment of MDA-MB-231 cells, that normally produce twice the amount of cell-surface HSPGs, promotes their responsiveness to FGF (Delehedde, M et al., 1996, *Exp Cell Res* 229: 398-406. Since FGF binds heparin and is known to be closely modulated by HSPGs, this suggests a close relationship between FGF responsiveness and HSPG expression levels. Furthermore, it has been shown recently that the metastatic potential of tumor cells can be greatly enhanced by the expression of endogenous heparanases (Vlodavsky, I. et al., 1999, *Nat Med* 5:793-802), that levels of a prominent HSPG, syndecan-1, is reduced in metastatic tumors (Stanley, M J et al., 1999, *Am J Clin Pathol* 112:377-383), and that low molecular weight heparin compounds can actually reduce the metastatic potential of melanoma cells by blocking endogenous heparanases (Miao, H Q et al., 1999, *Int J Cancer* 83:424-431). In view of the foregoing, the present invention is used to differentially target peptides or polypeptides to HSPGs, to modulate HSPG levels by the $P_{trg}$ fused to the targeting N-HBD, to inhibit endogenous heparanases, to raise syndecan-1 levels, and the like.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and re-ligated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA or genomic DNA libraries. However, once the sequence is disclosed it is possible to synthesize the entire gene sequence in vitro starting from the individual nucleotide derivatives. The entire gene sequence for genes of sizeable length, e.g., 500-1000 bp may be prepared by synthesizing individual overlapping complementary oligonucleotides and filling in single stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al., *Science* (1984) 223:1299; and Jay, E., *J Biol Chem* (1984) 259:6311.

Synthetic oligonucleotides are prepared by either the phosphotriester method as described by references cited above or the phosphoramidite method as described by Beaucage, S. L., and Caruthers, M H, *Tetrahed. Lett.* (1981) 22:1859; and Matteucci, M. D., and Caruthers, M. H., *J Am Chem Soc* (1981) 103:3185 and can be prepared using commercially available automated oligonucleotide synthesizers. Kinase treatment of single strands prior to annealing or for labeling is achieved using an excess of polynucleotide kinase.

Once the components of the desired vectors are thus available, they can be excised and ligated using standard restriction and ligation procedures. Site-specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 mg of plasmid or DNA sequence is cleaved by one unit of enzyme in about 20 ml of buffer solution; in the examples herein, typically, an excess of restriction enzyme is used to insure complete digestion of the DNA substrate. Incubation times of about one hr to two hrs at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499-560.

Restriction cleaved fragments may be blunt ended by treating with the large fragment of *E. coli* DNA polymerase I (Klenow) in the presence of the four deoxynucleotide triphosphates (dNTPs) using known incubation times and concentrations of dNTPs, salts and buffers. The Klenow fragment fills in at 5' single-stranded overhangs but chews back protruding 3' single strands, even though the four dNTPs are present. If desired, selective repair can be performed by supplying only one of the, or selected, dNTPs within the limitations dictated by the nature of the overhang. After treatment with Klenow, the mixture is extracted and ethanol precipitated. Treatment under appropriate conditions with S1 nuclease or BAL-31 results in hydrolysis of any single-stranded portion.

Ligations are typically performed in 15-50 ml volumes under the standard conditions and temperatures. Intermolecular "sticky end" ligations are usually performed at 33-100 μg/ml total DNA concentrations (5-100 nM total end concentration). Intermolecular blunt end ligations are performed at 1 mM total ends concentration.

In vector construction employing "vector fragments", the fragment is commonly treated with bacterial alkaline phosphatase or calf intestinal alkaline phosphatase in order to remove the 5' phosphate and prevent self-ligation. Digestions are conducted at pH 8 and the preparation extracted with phenol/chloroform and ethanol precipitated. Alternatively, re-ligation can be prevented in vectors which have been double digested by additional restriction enzyme and separation of the unwanted fragments.

Any of a number of methods are used to introduce mutations into the coding sequence to generate desired amino acid sequence variants of the invention. These mutations include simple deletions or insertions, systematic deletions, insertions or substitutions of clusters of bases or substitutions of single bases.

For example, modifications of N-HBD DNA sequence (cDNA or genomic DNA) are created by site-directed mutagenesis, a well-known technique for which protocols and reagents are commercially available (Zoller, M J et al., *Nucleic Acids Res* (1982) 10:6487-6500 and Adelman, J P et al., *DNA* (1983) 2:183-193)). Correct ligations for plasmid construction are confirmed, for example, by first transforming *E. coli* strain MC1061 (Casadaban, M., et al., *J Mol Biol* (1980) 138:179-207) or other suitable host with the ligation mixture. Using conventional methods, transformants are selected based on the presence of the ampicillin-, tetracycline- or other antibiotic resistance gene (or other selectable marker) depending on the mode of plasmid construction. Plasmids are then prepared from the transformants with optional chloramphenicol amplification optionally following chloramphenicol amplification ((Clewell, D B et al., *Proc Natl Acad Sci USA* (1969) 62:1159; Clewell, D. B., *J Bacteriol* (1972) 110:667). Several mini DNA preps are commonly used. See, e.g., Holmes, D S, et al., *Anal Biochem* (1981) 114:193-197; Birnboim, H C et al., *Nucleic Acids Res* (1979) 7:1513-1523. The isolated DNA is analyzed by restriction and/or sequenced by the dideoxy nucleotide method of Sanger (*Proc Natl Acad Sci USA* (1977)74:5463) as further described by Messing, et al., *Nucleic Acids Res* (1981) 9:309, or by the method of Maxam et al. *Methods in Enzymology* (1980) 65:499.

Vector DNA can be introduced into mammalian cells via conventional techniques such as calcium phosphate or calcium chloride co-precipitation, DEAE-dextran-mediated transfection, lipofection, or electroporation. Suitable methods for transforming host cells can be found in Sambrook et al. supra and other standard texts.

Often, in fusion expression vectors, a proteolytic cleavage site is introduced at the junction of the reporter group and the target protein to enable separation of the target protein from the reporter group subsequent to purification of the fusion protein. Proteolytic enzymes for such cleavage and their recognition sequences include Factor Xa, thrombin and enterokinase.

Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase, maltose E binding protein, or protein A, respectively, to the target recombinant protein.

Promoters and Enhancers

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Suitable promoters may be inducible, repressible or constitutive. An example of a constitutive promoter is the viral promoter MSV-LTR, which is efficient and active in a variety of cell types, and, in contrast to most other promoters, has the same enhancing activity in arrested and growing cells. Other preferred viral promoters include that present in the CMV-LTR (from cytomegalovirus) (Bashart, M. et al., *Cell* 41:521 (1985)) or in the RSV-LTR (from Rous sarcoma virus) (Gorman, C. M., *Proc. Natl. Acad. Sci. USA* 79:6777 (1982). Also useful are the promoter of the mouse metallothionein I gene (Hamer, D., et al., *J. Mol. Appl. Gen.* 1:273-288 (1982)); the TK promoter of Herpes virus (McKnight, S., *Cell* 31:355-365 (1982)); the SV40 early promoter (Benoist, C., et al., *Nature* 290:304-310 (1981)); and the yeast gal4 gene promoter (Johnston, S. A., et al., *Proc. Natl. Acad. Sci. (USA)* 79:6971-6975 (1982); Silver, P. A., et al., *Proc. Natl. Acad. Sci. (USA)* 81:5951-5955 (1984)). Other illustrative descriptions of transcriptional factor association with promoter regions and the separate activation and DNA binding of transcription factors include: Keegan et al., *Nature* (1986) 231:699; Fields et al., *Nature* (1989) 340:245; Jones, *Cell* (1990) 61:9; Lewin, Cell (1990) 61:1161; Ptashne et al., *Nature* (1990) 346:329; Adams et al., *Cell* (1993) 72:306. The relevant disclosure of all of these above-listed references is hereby incorporated by reference.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed in (Roy-Burman et al., U.S. Pat. No. 5,112,767). For a general discussion of enhancers and their actions in transcription, see, Lewin, B M, *Genes IV,* Oxford University Press, Oxford, (1990), pp. 552-576. Particularly useful are retroviral enhancers (e.g., viral LTR). The enhancer is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency on the DNA molecule of the present invention.

The nucleic acid sequences of the invention can also be chemically synthesized using standard techniques. Various methods of chemically synthesizing polydeoxynucleotides are known, including solid-phase synthesis which, like peptide synthesis, has been fully automated with commercially available DNA synthesizers (See, e.g., Itakura et al. U.S. Pat. No. 4,598,049; Caruthers et al. U.S. Pat. No. 4,458,066; and Itakura U.S. Pat. Nos. 4,401,796 and 4,373,071, incorporated by reference herein).

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42C. Another example is use of 50% formamide, 5×SSC (0.75 M NaCl, 0.075 M sodium citrate), 50 mM sodium phosphate (pH 6/8), 0.1% sodium pyrophosphate, 5× Denhardt's solution, sonicated salmon sperm DNA (50 μg/ml), 0.1% SDS, and 10% dextran sulfate at 42° C., with washes at 42C. in 0.2×SSC and 0.1% SDS. Yet another example is hybridization using a buffer of 10% dextran sulfate, 2×SSC and 50% formamide at 55° C., followed by a high-stringency wash consisting of 0.1×SSC containing EDTA at 55° C.

Proteins and Polypeptides

The present invention includes an "isolated" N-HBD polypeptide from human NRG having the sequence

```
                                            (SEQ ID NO:1)
GSKLVLRCET SSEYSSLRFK WFKNGNELNR KNKPQNIKIQ

KKPGKSELRI NKASLADSGE YMCKVISKLG
``` or, preferably, a fusion polypeptide thereof.

A preferred fragment of the above sequence is the fragment rich in basic amino acids: KWFKNGNELNRKNKPQNIKIQKKPGK (SEQ ID NO:7) which would have a relative high affnity for the basic heparan sulfates to which the sequence is intended to be targeted.

The amino acid sequence of the rat N-HBD homologue within rat NRG is

```
                                           SEQ ID NO:2
GSKLVLRCET SSEYSSLRFK WFKNGNELNR KNKPENIKIQ

KKPGKSELRI NKASLADSGE YMCKVISKLG.
```

A preferred fragment of the above sequence is the fragment rich in basic amino acids: KWFKNGNELNRKNKPENIKIQKKPGK (SEQ ID NO:8) which would have a relative high affinity for the basic heparan sulfates to which the sequence is intended to be targeted.

Homologous chicken sequences were used by the present inventor in the Examples herein. The N-HBD of chicken NRG is (SEQ ID NO:3)
GQKLVLRCET TSEYPALRK• WLKNGKEITK KNRPENVKIP

KKQKKYSELHI YRATLADAGE YACRVSSKLG

As with the human and rat sequence, a preferred fragment of the above sequence is the fragment rich in basic amino acids: KWLKNGKEITKKNRPENVKIPKKQKK (SEQ ID NO:9)

Another preferred functional derivative is a polypeptide having the sequence K-x-x-K-x-x-x-x-x-x-R-K-x-K-x-x-x-x-K-x-x-K-K-x-x-K (SEQ ID NO:10), wherein x is any amino acid, or a fragment of SEQ ID NO:10 that includes at least four, preferably at least six Lys and/or Arg residues.

While the present disclosure exemplifies the use of fragments of the full length chicken NRG, namely the N-HBD and the EGF-like domain, at the protein and DNA levels, it is to be understood human homologues of the chicken sequences (e.g., SEQ ID NO:1 and 7, and the N-HBD from other mammalian species and mutants thereof that possess the characteristics disclosed herein are intended within the scope of this invention.

Also included is a "functional derivative" of N-HBD which is means an amino acid substitution variant (=mutant), a "fragment," or a "chemical derivative" of N-HBD, which terms are defined below. A functional derivative retains measurable N-HBD activity, preferably that of binding to heparin, heparan sulfate or a heparan sulfate proteoglycan (HSPG) in solution or HSPG on the surface of cells, which permits its utility in accordance with the present invention.

"Functional derivatives" encompass mutants, "variants" and "fragments" regardless of whether the terms are used in the conjunctive or the alternative herein.

A functional homologue must possess the above biochemical and biological activity. In view of this functional characterization, use of homologous N-HBD polypeptides from other species, including polypeptides not yet discovered, fall within the scope of the invention if these polypeptides have sequence similarity and the recited biochemical and biological activity.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred method of alignment, Cys residues are aligned.

In a preferred embodiment, the length of a sequence being compared is at least 30%, preferably at least 40%, more preferably at least 50%, even more preferably at least 60%, and even more preferably at least 70%, 80%, or 90% of the length of the reference sequence. For example, when aligning a second sequence to the human N-HBD amino acid sequence (SEQ ID NO:2) having 276 amino acid residues, at least 83, preferably at least 110, more preferably at least 138, even more preferably at least 166, and even more preferably at least 193, 221 or 248 amino acid residues are aligned). The amino acid residues (or nucleotides) at corresponding amino acid positions (or nucleotide) positions are then compared. When a position in the first sequence is occupied by the same amino acid residue (or nucleotide) as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (J. Mol. Biol. 48:444-453 (1970) algorithm which has been incorporated into the GAP program in the GCG software package (available at the Worldwide Web URL: gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (see, Worldwide Web URL, supra), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4.

The nucleotide and amino acid sequences of the present invention can further be used as a "query sequence" to perform a search against public databases, for example, to identify other family members or related sequences. Such searches can be performed using the NBLAST and XBLAST programs (version 2.0) of Altschul et at. (1990) J. Mol. Biol. 215:403-10. BLAST nucleotide searches can be performed with the NBLAST program, score=100, wordlength=12 to obtain nucleotide sequences homologous to, e.g., human or chicken N-HBD nucleic acid molecules. BLAST protein searches can be performed with the XBLAST program, score=50, wordlength=3 to obtain amino acid sequences homologous to human or murine N-HBD protein molecules of the invention. To obtain gapped alignments for comparison purposes, Gapped BLAST can be utilized as described in Altschul et al. (1997) Nucleic Acids Res. 25:3389-3402. When utilizing BLAST and Gapped BLAST programs, the default parameters of the respective programs (e.g., XBLAST and NBLAST) can be used. See the Worldwide Web URL: ncbi.nlm.nih.gov.

Thus, a homologue of the N-HBD protein described above is characterized as having (a) functional activity of a reference N-HBD polypeptide, and (b) sequence similarity to a reference N-HBD polypeptide (such as SEQ ID NO:1 or SEQ ID NO:2 when determined above, of at least about 30% (at the amino acid level), preferably at least about 50%, more preferably at least about 70%, even more preferably at least about 90%.

It is within the skill in the art to obtain and express such a polypeptide using DNA probes based on the disclosed sequences of N-HBD and the published full length sequences of NRG that include flanking nucleotide sequence. Then, the polypeptide's biochemical and biological activity can be tested readily using art-recognized methods such as those described herein, for example, binding to cells or ECM via recognition of the heparan sulfate component of HSPGs associated with cell surfaces and with ECM. Such binding will indicate whether the homologue has the requisite activity to qualify as a "functional" homologue.

Preferred assays measure the functional characteristics of N-HBD which can be "simulated" by binding to the synthetic ligand heparin or assessed by measuring binding to its "natural" ligand heparan sulfate. As exemplified herein, binding of N-HBD (or a fusion protein thereof) to its natural ligand(s) on, for example, muscle cells, permits an associated polypeptide, namely the EGF-like domain of NRG, to transmit a signal via the tyrosine kinase receptor (erbB4). Any relevant downstream event can be measured whether by biochemical means (e.g., phosphorylation) or by a cellular assay, or a physiologic or pharmacologic assay. As noted above, such binding to muscle cells promotes the transition of AChRs from an embryonic to an adult forms by inducing the switch to the α-AChR subunit and the expression of voltage-gated sodium channels. As exemplified herein, one such event is an increased insertion rate of new AChRs into the membrane. Moreover, for the engineered fusion proteins of this invention that comprise an N-HBD or functional derivative, any assay appropriate for measuring the action of the fusion partner ($P_{trg}$ as defined herein) can be used.

All the polypeptides, fusion polypeptides or other functional derivatives and chemical derivatives including peptidomimetics and multimeric peptides described herein preferably have at least about 20% of the activity of native N-HBD in an in vitro assay. Alternatively, or in addition, these derivatives should compete with labeled N-HBD polypeptide (with an $IC_{50} \leqq 10$ μM, more preferably $\leqq 1$ μM) for binding to a ligand or binding partner, preferably heparin or HSPG when tested in a binding assay with whole cells, cell fractions, isolated HSPG or heparin.

A mutant or "variant" of N-HBD refers to a molecule substantially identical to either the full protein or to a fragment thereof in which one or more amino acid residues have been replaced (substitution variant) or which has one or several residues deleted (deletion variant) or added (addition variant). A "fragment" of N-HBD refers to any subset of the molecule, preferably one that includes the ECD, that is, a shorter polypeptide of the full-length protein.

A number of processes can be used to generate fragments, mutants and variants of the isolated DNA sequence. Small subregions or fragments of the nucleic acid encoding the N-HBD protein, for example 1-30 bases in length, can be prepared by standard, chemical synthesis. Antisense oligonucleotides and primers for use in the generation of larger synthetic fragment.

Fusion Polypeptides and Linkers

As noted above, a preferred functional derivative is a fusion protein, a polypeptide that includes a functional fragment of N-HBD fused or linked to a $P_{trg}$.

The N-HBD or derivative may be linked to the $P_{trg}$ by any type of linker moiety known in the art, e.g., a stretch of Gly residues, a peptide linker comprising various amino acids, or a chemical cross-linking moiety. A preferred linker is one that is cleavable by an enzyme that is present and active in the vicinity of, the cell surface or ECM to which the $P_{trg}$ is being targeted, e.g., at a tumor site. The N-HBD would be released from the therapeutic $P_{trg}$ when the enzyme acts on the fusion polypeptide. Preferred enzymes are a matrix metalloprotease, urokinase, a cathepsin, plasmin or thrombin, which can act to release the $P_{trg}$ in vivo (or in situ) in the tumor milieu. Preferred linkers of this type are peptides having the sequence VPRGSD (SEQ ID NO:11) or DDKDWH {SEQ ID NO:12).

Multidomain and Multimeric Peptide Fusion Proteins

The present invention also includes longer polypeptides in which a "unit" peptidic sequence obtained from the sequence of N-HBD or a variant thereof is repeated from about two to about 100 times, with or without intervening spacers or linkers.

A multimer of the peptide referred to symbolically in this section as HBD is shown by the following formula $(\underline{HBD}\text{-}X_m)_n\text{-}\underline{HBD}$ wherein m=0 or 1, n=1-100. X is a spacer group, consisting of 1-20 glycine residues, a peptide linker as described above, or a chemical cross-linking moiety.

A preferred HBD unit of such a multimer is KWFKNGNELNRKKPQNIKIQKKPGK SEQ ID NO:7, or a functional fragment thereof.

Another preferred functional derivative is a polypeptide having the sequence K-x-x-K-x-x-x-x-x-x-R-K-x-K-x-x-x-x-K-x-x-K-K-x-x-K (SEQ ID NO:10), wherein x is any amino acid, or a fragment of SEQ ID NO:10 that includes at least six Lys or Arg residues. In a more generic version of the above polypeptide, any basic amino acid residue can substitute at the positions occupied by Lys or Arg in SEQ ID NO:10.

It is understood that even if the basic subunit of the multimer has relatively low heparin-binding affinity, the multimer will have increased affinity and/or avidity to the target structure, thereby enabling the use of the multimer in accordance with this invention.

It is also understood that such multimers may be built from any of the peptide variants defined herein. Moreover, a peptide multimer may comprise different combinations of non-identical peptide monomers and the disclosed substitution variants thereof. Such oligomeric or multimeric peptides can be made by chemical synthesis or by recombinant DNA techniques as discussed herein. When produced chemically, the oligomers preferably have from 2-8 repeats of the monomer sequence. When produced recombinantly, the multimers may have as many repeats as the expression system permits, for example from two to about 100 repeats.

In tandem multimers, preferably dimers and trimers, of the N-HBD peptide or polypeptide, the chains bonded by interchain disulfide bonds or other "artificial" covalent bonds between the chains such that the peptide units are "side-by-side" rather than "end-to-end."

Multimers may also include more than one repeat of $P_{trg}$ or a functional derivative thereof that has similar biologic and pharmacologic activity to that of the $P_{trg}$. More than one type of $P_{trg}$ may be combined in a single fusion polypeptide. In this regard, an antigen binding domain of an antibody (Ab) molecule may be fused with an N-HBD and another $P_{trg}$ to result in an Ab:N-HBD:$P_{trg}$ fusion product. Such a polypeptide adds the Ab's selectivity to the delivery mediated by the N-HBD and the desired biological activity provided by the $P_{trg}$. Thus, for example, the Ab may be specific for a tumor cell surface antigen (as is the case with Her2/Neu mAbs used in cancer therapy) so that once the fusion construct is concentrated in the ECM by the N-HBD, the activity may be focused onto tumor cells within that milieu. The Ab domain is preferably introduced into the fusion construct at the DNA level by use of a nucleic acid encoding an Ab Fab fragment, Fv fragment (Hochman, J. et al. (1973) Biochemistry 12:1130-1135; Sharon, J, et al.(1976) Biochemistry 15:1591-1594) a "single-chain antibody" (scFv; also termed "scAb"). The latter is a single chain polypeptide molecule wherein an Ig $V_H$ domain and an Ig $V_L$ domain are artificially linked by a short peptide linker that allows the scFv to assume a conformation which retains specificity and binding capacity for the antigen (or epitope) against which the original antibody (from which the $V_H$ and $V_L$ domains are derived) was specific. See, for example, Skerra, A. et al. (1988) *Science,* 240: 1038-1041; Pluckthun, A. et al. (1989) *Methods Enzymol.* 178: 497-515; Winter, G. et al. (1991) *Nature,* 349: 293-299); Bird et al., (1988) *Science* 242:423; Huston et al. (1988) *Proc. Natl. Acad. Sci. USA* 85:5879; U.S. Pat. Nos. 4,704,692, 4,853,871, 4,946,778, 5,260,203, 5,455,030.

A "soluble N-HBD" is a cell-free form of N-HBD that may be shed, secreted or otherwise extracted from the producing cells. Soluble N-HBD preferably includes soluble fusion proteins wherein the N-HBD is fused genetically or conjugated chemically to a biologically active molecule, such as a $P_{trg}$.

A preferred group of N-HBD variants are those in which at least one amino acid residue and preferably, only one, has been substituted by different residue. For a detailed description of protein chemistry and structure, see Schulz, G E et al., *Principles of Protein Structure,* Springer-Verlag, New York, 1978, and Creighton, T. E., *Proteins: Structure and Molecular Properties,* W. H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| 1 | Small aliphatic, nonpolar or slightly polar residues | Ala, Ser, Thr (Pro, Gly); |
|---|---|---|
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

More substantial changes in biochemical, functional (or immunological) properties are made by selecting substitutions that are less conservative, such as between, rather than within, the above five groups. Such changes will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of such substitutions are (i) substitution of Gly and/or Pro by another amino acid or deletion or insertion of Gly or Pro; (ii) substitution of a hydrophilic residue, e.g., Ser or Thr, for (or by) a hydrophobic residue, e.g., Leu, Ile, Phe, Val or Ala; (iii) substitution of a Cys residue for (or by) any other residue; (iv) substitution of a residue having an electropositive side chain, e.g., Lys, Arg or His, for (or by) a residue having an electronegative charge, e.g., Glu or Asp; or (v) substitution of a residue having a bulky side chain, e.g., Phe, for (or by) a residue not having such a side chain, e.g., Gly.

Most preferred deletions, insertions and substitutions according to the present invention are those that do not produce radical changes in the characteristics of the N-HBD protein, maintaining its activity. However, when it is difficult to predict the exact effect of the substitution, deletion or insertion in advance of doing so, one skilled in the art will appreciate that the effect can be evaluated by routine screening assays such as those described here, without requiring undue experimentation.

Whereas shorter chain variants can be made by chemical synthesis, for the present invention, the preferred longer chain variants are typically made by site-specific mutagenesis of the nucleic acid encoding the N-HBD polypeptide, expression of the variant nucleic acid in cell culture, and, optionally, purification of the polypeptide from the cell culture, for example, by immunoaffinity chromatography using specific antibody immobilized to a column (to absorb the variant by binding to at least one epitope).

Chemical Derivatives of N-HBD

"Chemical derivatives" of N-HBD contain additional chemical moieties not normally a part of the protein. Covalent modifications of the polypeptide are included within the scope of this invention. Such derivatized moieties may improve the solubility, absorption, biological half life, and the like. Moieties capable of mediating such effects are disclosed, for example, in *Remington's Pharmaceutical Sciences,* 16th ed., Mack Publishing Co., Easton, Pa. (1980).

Such modifications may be introduced into the molecule by reacting targeted amino acid residues of the polypeptide with an organic derivatizing agent that is capable of reacting with selected side chains or terminal residues. Another modification is cyclization of the protein.

Examples of chemical derivatives of the polypeptide are provided below. Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79-86), acetylation of the N-terminal amine, and amidation of the C-terminal carboxyl groups.

Also included are peptides wherein one or more D-amino acids are substituted for one or more L-amino acids.

Peptidomimetics

Another class of compounds useful in this regard are low molecular weight peptidomimetic compounds which mimic the activity of an N-HBD polypeptide. Structure of such peptidomimetics may be derived from the structure of either the free N-HBD or N-HBD bound to its ligand, e.g., heparan sulfate.

A peptidomimetic of N-HBD mimics the biological effect of a N-HBD peptide and may be an unnatural peptide or a non-peptide agent which has the stereochemical properties of a N-HBD peptide such that it has the binding activity or biological activity of the peptide. Hence, this invention includes compounds wherein a peptidomimetic compound is coupled to another peptide.

A peptidomimetic agent may be an unnatural peptide or a non-peptide agent which recreates the stereospatial properties of the binding elements of N-HBD such that it has the binding activity or biological activity of N-HBD. Similar to the linear peptides corresponding to N-HBD, a peptidomimetic will have a binding face (which interacts with heparan sulfate) and a non-binding face. Again, similar to linear peptides of N-HBD, the non-binding face of a peptidomimetic will contain functional groups that can be modified by various therapeutic moieties without modifying the binding face of the peptidomimetic. A preferred embodiment of a peptidomimetic would contain an aniline on the non-binding face of the molecule. The $NH_2$-group of an aniline has a pKa~4.5 and could therefore be modified by any $NH_2$-selective reagent without modifying any $NH_2$ functional groups on the binding face of the peptidomimetic. Other peptidomimetics may not have any $NH_2$ functional groups on their binding face and therefore, any $NH_2$, without regard for $pK_a$ could be displayed on the non-binding face as a site for conjugation. In addition other modifiable functional groups, such as —SH and —COOH could be incorporated into the non-binding face of a peptidomimetic as a site of conjugation. A therapeutic moiety could also be directly incorporated during the synthesis of a peptidomimetic and preferentially be displayed on the non-binding face of the molecule.

This invention also includes compounds, which retain partial peptide characteristics. For example, any proteolytically unstable bond within a peptide of the invention could be selectively replaced by a non-peptidic element such as an isostere (N-methylation; D-amino acid at a particular site) or a reduced peptide bond while the rest of the molecule retains its peptide nature.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V J, *Biopolymers* 33:1073-1082 (1993); Wiley, R. A. et al., *Med. Res. Rev.* 13:327-384 (1993); Moore et al., *Adv. in Pharmacol* 33:91-141 (1995); Giannis et al., *Adv. in Drug Res.* 29:1-78 (1997), which references are incorporated by reference in their entirety). These methods are used to make peptidomimetics that possess at least the binding capacity and specificity of N-HBD peptides and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the cystallographically-derived three-dimensional structure of a peptide of the invention either free or bound in complex. Alternatively, the structure of a peptide of the invention bound to its ligand can be gained by using nuclear magnetic resonance spectroscopy. The better knowledge of the stereochemistry of the interaction of a peptide with its ligand will contribute to the rational design of such peptidomimetic agents.

Engineering of Polypeptides with Improved Specificity and Affinity

Mutants or variant HBD sequences, whether in the form of polypeptides, fusion polypeptides, multimers, etc., with increased binding activity (defined as increased specificity, affinity or both) for a target HSPG or other sugar can be produced and tested using the methods described herein and known in the art. Thus, one screens the binding specificity or affinity of a candidate variant or mutant HBD on oligosaccharide arrays to determine the optimal sugar structures that bind to that HBD. With that information in hand, one can screen a peptide library of the HBD or, in a directed manner, mutate selected residues in the HBD, and screen these mutants for binding to, for example, a tissue array. This generates HBD modules that are characterized in that they bind to specific saccharide moieties expressed on specific tissues or cells. In this way, variant HBDs with improved binding activity for particular targets, e.g., tumors, can be identified and used to engineer better antagonists, such as HBD-containing fusion polypeptides, for that particular target. Methods for preparing and using tissue arrays are described by Richter J et al., 2000, *Am J Pathol* 157:787-794; Fernandez PL et al., *Virchows Arch* 438:591-594; and Simon R et al., 2001, *Cancer Res* 61:4514-4519). Tissue binding studies of heparin-binding proteins are described in Allen B L et al., 2001, *J Cell Biol* 155:845-858; Friedl A et al., 2001, *Methods Mol Biol* 171:535-546; Rapraeger A C, 2002, *Meth Cell Biol* 69:83-109. Thus the present invention includes methods for identifying an HBD with optimal tissue specificity and for making tissue-specific targeting vectors which may be antagonists of a selected biological function. Testing in the appropriate tissue culture system or animal model is performed to determine effectiveness of targeting, toxicity and biological function of the engineered HBD.

Therapeutic Compositions and Their Administration

The N-HBD fusion polypeptide or a cell expressing this polypeptide is administered to a mammalian subject, preferably a human. A composition having the activity of N-HBD as described herein is administered in a pharmaceutically acceptable carrier in a biologically effective or a therapeutically effective amount. The N-HBD fusion polypeptide (or cell expressing the polypeptide) may be given alone or in combination with another protein, peptide or other drug.

The N-HBD fusion polypeptide that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

A composition of this invention may be active per se, or may act as a "pro-drug" that is converted in vivo to the active form.

Compositions within the scope of this invention include all compositions wherein the N-HBD fusion polypeptide, functional derivative, etc. is contained in an amount as defined below that is effective to achieve its intended purpose. The following doses and amounts also pertain to the antibodies of the invention when administered to a subject. A therapeutically effective amount is a dosage that, when given for an effective period of time, achieves the desired pharmacological or clinical effect.

A therapeutically active amount of a polypeptide having N-HBD activity may vary according to factors such as the disease state, age, sex, and weight of the individual, and the ability of the polypeptide to elicit a desired response in the individual. Dosage regimes may be adjusted to provide the optimum therapeutic response. For example, several divided doses may be administered daily or the dose may be proportionally reduced as indicated by the exigencies of the therapeutic situation. A therapeutically effective amounts of the protein, in cell associated form may be stated in terms of the protein or cell equivalents.

Thus an effective amount is between about 1 ng and about 1 gram per kilogram of body weight of the recipient, more preferably between about 1 µg and 100 mg/kg, more preferably, between about 100 µg and about 100 mg/kg. Dosage forms suitable for internal administration preferably contain (for the latter dose range) from about 0.1 mg to 500 mg of active ingredient per unit. The active ingredient may vary from 0.5 to 95% by weight based on the total weight of the composition. Alternatively, an effective dose of cells expressing N-HBD, such as transduced cells is between about $10^4$ and $10^9$ cells, more preferably between about $10^6$ and $10^8$ cells per subject, preferably in split doses. Those skilled in the relevant therapeutic arts will be able to adjust these doses without undue experimentation.

The active compound, e.g., N-HBD fusion polypeptide or cell transduced with N-HBD DNA, may be administered in a convenient manner, e.g., injection or infusion, by a convenient and effective route. Preferred routes include subcutaneous, intradermal, intravenous and intramuscular routes. Other possible routes include oral administration, intracerebroventricular, intrathecal, inhalation, transdermal application, or rectal administration. For the treatment of tumors which have not been completely resected, direct intratumoral injection is also intended.

Depending on the route of administration, the active compound may be coated in a material to protect the compound from the action of enzymes, acids and other natural conditions which may inactivate the compound. Thus, to a administer a polypeptide or peptide having N-HBD activity by an enteral route, it may be necessary to coat the composition with, or co-administer the composition with, a material to prevent its inactivation. For example, a peptide may be administered to an individual in an appropriate carrier, diluent or adjuvant, co-administered with enzyme inhibitors (e.g., pancreatic trypsin inhibitor, diisopropylfluoro-phosphate (DFP) and trasylol). or in an appropriate carrier such as liposomes (including water-in-oil-in-water emulsions as well as conventional liposomes (Strejan et al., (1984) *J. Neuroimmunol* 7:27).

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Prolonged absorption of the injectable compositions can be brought about by including in the composition an agent which delays absorption, for example, aluminum monostearate and gelatin.

Parenteral compositions are preferably formulated in dosage unit form for ease of administration and uniformity of dosage. Dosage unit form refers to physically discrete units suited as unitary dosages for a mammalian subject; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

For topical application, the proteins of the present invention may be incorporated into topically applied vehicles such as salves or ointments, which have both a soothing effect on the skin as well as a means for administering the active ingredient directly to the affected area.

The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

Other pharmaceutically acceptable carriers for the N-HBD fusion polypeptide according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

Delivery of DNA Encoding N-HBD Fusion Polypeptide

DNA delivery to animals, for example to effect what is generally known as "gene therapy," or to cells ex vivo, involves introduction of a "foreign" DNA into a cell and ultimately, into a live animal. As used herein, the term "gene therapy" is not intended to be limited to the correction or replacement of a deficient gene in vivo, rather, the delivery of a DNA molecule of the present invention (not necessarily a "gene") in a manner permitting it expression and thereby, its utility as described. Several general strategies for gene therapy have been studied and have been reviewed extensively (Yang, N-S, *Crit. Rev. Biotechnol.* 12:335-356 (1992); Anderson, W. F., *Science* 256:808-813 (1992); Miller, A S, *Nature* 357:455-460 (1992); Crystal, R G, *Amer. J. Med.* 92(suppl 6A):44S-52S (1992); Zwiebel, J A et al., *Ann. N.Y. Acad. Sci.* 618:394-404 (1991); McLachlin, J R et al., *Prog. Nucl. Acid Res. Molec. Biol.* 38:91-135 (1990); Kohn, D B et al., *Cancer Invest.* 7:179-192 (1989), which references are herein incorporated by reference in their entirety). One approach comprises nucleic acid transfer into primary cells in culture followed by autologous transplantation of the ex vivo transformed cells into the host, either systemically or into a particular organ or tissue.

For accomplishing the objectives of the present invention, nucleic acid therapy would be accomplished by direct transfer of a the functionally active DNA into mammalian somatic tissue or organ in vivo. DNA transfer can be achieved using a number of approaches described below. These systems can be tested for successful expression in vitro by use of a selectable marker (e.g., G418 resistance) to select transfected clones expressing the DNA, followed by detection of the presence of the N-HBD expression product (after treatment with the inducer in the case of an inducible system) using an antibody to the product in an appropriate immunoassay. Efficiency of the procedure, including DNA uptake, plasmid integration and stability of integrated plasmids, can be improved by linearizing the plasmid DNA using known methods, and co-transfection using high molecular weight mammalian DNA as a "carrier".

Examples of successful "gene transfer" reported in the art include: (a) direct injection of plasmid DNA into mouse muscle tissues, which led to expression of marker genes for an indefinite period of time (Wolff, J A et al., *Science* 247:1465 (1990); Acsadi, G et al., *The New Biologist* 3:71 (1991)); (b) retroviral vectors are effective for in vivo and in situ infection of blood vessel tissues; (c) portal vein injection and direct injection of retrovirus preparations into liver effected gene transfer and expression in vivo (Horzaglou, M. et al., *J. Biol. Chem.* 265:17285 (1990); Koleko, M. et al., *Human Gene Therapy* 2:27 (1991); Ferry, N. et al., *Proc. Natl. Acad. Sci. USA* 88:8387 (1991)); (d) intratracheal infusion of recombinant adenovirus into lung tissues was effective for in vivo transfer and prolonged expression of foreign genes in lung respiratory epithelium (Rosenfeld, M A et al., *Science* 252: 431 (1991); (e) Herpes simplex virus vectors achieved in vivo gene transfer into brain tissue (Ahmad, F. et al., eds, *Miami Short Reports-Advances in Gene Technology: The Molecular Biology of Human Genetic Disease*, Vol 1, Boehringer Mannheim Biochemicals, USA, 1991).

Retroviral-mediated human therapy utilizes amphotrophic, replication-deficient retrovirus systems (Temin, H M, *Human Gene Therapy* 1:111 (1990); Temin et al., U.S. Pat. No. 4,980,289; Temin et al., U.S. Pat. No. 4,650,764; Temin et al., U.S. Pat. No. 5,124,263; Wills, J W, U.S. Pat. No. 5,175,099; Miller, A D, U.S. Pat. No. 4,861,719). Such vectors have been used to introduce functional DNA into human cells or tissues, for example, the adenosine deaminase gene into lymphocytes, the NPT-II gene and the gene for tumor necrosis factor into tumor infiltrating lymphocytes. Retrovirus-mediated gene delivery generally requires target cell proliferation for gene transfer (Miller, D G et al., *Mol. Cell. Biol.* 10:4239 (1990). This condition is met by certain of the preferred target cells into which the present DNA molecules are to be introduced, i.e., actively growing tumor cells. Gene therapy of cystic fibrosis using transfection by plasmids using any of a number of methods and by retroviral vectors has been described by Collins et al., U.S. Pat. No. 5,240,846.

The DNA molecules encoding the N-HBD sequences may be packaged into retrovirus vectors using packaging cell lines that produce replication-defective retroviruses, as is well-known in the art (see, for example, Cone, R. D. et al., *Proc. Natl. Acad. Sci. USA* 81:6349-6353 (1984); Mann, R F et al., *Cell* 33:153-159 (1983); Miller, A D et al., *Molec. Cell. Biol.* 5:431-437 (1985),; Sorge, J, et al., *Molec. Cell. Biol.* 4:1730-1737 (1984); Hock, R A et al., *Nature* 320:257 (1986); Miller, A D et al., *Molec. Cell. Biol.* 6:2895-2902 (1986). Newer packaging cell lines which are efficient an safe for gene transfer have also been described (Bank et al., U.S. Pat. No. 5,278,056.

This approach can be utilized in a site specific manner to deliver the retroviral vector to the tissue or organ of choice. Thus, for example, a catheter delivery system can be used (Nabel, E G et al., *Science* 244:1342 (1989)). Such methods, using either a retroviral vector or a liposome vector, are particularly useful to deliver the nucleic acid to be expressed to a blood vessel wall, or into the blood circulation of a tumor.

Other virus vectors may also be used, including recombinant adenoviruses (Horowitz, M. S., In: *Virology*, Fields, B N et al., eds, Raven Press, New York, 1990, p. 1679; Berkner, K L, *Biotechniques* 6:616 9191988), Strauss, S E, In: *The Adenoviruses*, Ginsberg, H S, ed., Plenum Press, New York, 1984, chapter 11), herpes simplex virus (HSV) for neuron-specific delivery and persistence. Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., *EMBO J.* 10:3941 (1991) according to the present invention.

Another vector which can express the DNA molecule of the present invention, and is useful in the present therapeutic setting, particularly in humans, is vaccinia virus, which can be rendered non-replicating (U.S. Pat. Nos. 5,225,336; 5,204, 243; 5,155,020; 4,769,330; Sutter, G et al., *Proc. Natl. Acad. Sci. USA* (1992) 89:10847-10851; Fuerst, T R et al., *Proc. Natl. Acad. Sci. USA* (1989) 86:2549-2553; Falkner F G et al; *Nucl. Acids Res* (1987) 15:7192; Chakrabarti, S et al., *Molec. Cell. Biol.* (1985) 5:3403-3409). Descriptions of recombinant vaccinia viruses and other viruses containing heterologous DNA and their uses in immunization and DNA therapy are reviewed in: Moss, B., *Curr. Opin. Genet. Dev.* (1993) 3:86-90; Moss, B. *Biotechnology* (1992) 20: 345-362; Moss, B., *Curr Top Microbiol Immunol* (1992) 158:25-38; Moss, B., *Science* (1991) 252:1662-1667; Piccini, A et al., *Adv. Virus Res.* (1988) 34:43-64; Moss, B. et al., *Gene Amplif Anal* (1983) 3:201-213.

In addition to naked DNA or RNA, or viral vectors, engineered bacteria may be used as vectors. A number of bacterial strains including *Salmonella*, BCG and *Listeria monocytogenes*(LM) (Hoiseth et al., *Nature* 291, 238-239 (1981); Poirier, T P et al. *J. Exp. Med.* 168, 25-32 (1988); (Sadoff, J C, et al., *Science* 240, 336-338 (1988); Stover, C K et al., *Nature* 351, 456-460 (1991); Aldovini, A. et al., *Nature* 351, 479-482 (1991); Schafer, R., et al., *J. Immunol.* 149, 53-59 (1992); Ikonomidis, G. et al., *J. Exp. Med.* 180, 2209-2218 (1994)). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al., 1990, supra) and particle-bombardment mediated gene transfer (Yang, N.-S., et al., *Proc. Natl. Acad. Sci. USA* 87:9568 (1990); Williams, R S et al., *Proc. Natl. Acad. Sci. USA* 88:2726 (1991); Zelenin, A V et al., *FEBS Lett.* 280:94 (1991); Zelenin, A V et al., *FEBS Lett.* 244:65 (1989); Johnston, S A et al., *In Vitro Cell. Dev. Biol.* 27:11 (1991)). Furthermore, electroporation, a well-known means to transfer genes into cell in vitro, can be used to transfer DNA molecules according to the present invention to tissues in vivo (Titomirov, A V et al., *Biochim. Biophys. Acta* 1088:131 ((1991)).

"Carrier mediated" gene transfer (or DNA delivery) has also been described (Wu, CH et al., *J. Biol. Chem.* 264:16985 (1989); Wu, G Y et al., *J. Biol. Chem.* 263:14621 (1988); Soriano, P et al., *Proc. Natl. Acad. Sci. USA* 80:7128 (1983); Wang, C-Y. et al., *Proc. Natl. Acad. Sci. USA* 84:7851 (1982); Wilson, J M et al., *J. Biol. Chem.* 267:963 (1992)). Preferred carriers are targeted liposomes (Nicolau, C. et al., *Proc. Natl. Acad. Sci. USA* 80:1068 (1983); Soriano et al., supra) such as immunoliposomes, which can incorporate acylated mAbs into the lipid bilayer (Wang et al., supra). Polycations such as asialoglycoprotein/polylysine (Wu et al., 1989, supra) may be used, where the conjugate includes a molecule which recognizes the target tissue (e.g., asialoorosomucoid for liver) and a DNA binding compound to bind to the DNA to be transfected. Polylysine is an example of a DNA binding molecule which binds DNA without damaging it. This conjugate is then complexed with plasmid DNA according to the present invention for transfer.

Plasmid DNA used for transfection or microinjection may be prepared using methods well-known in the art, for example using the Quiagen procedure (Quiagen), followed by DNA purification using known methods, such as the methods exemplified herein.

Again, as noted above, for the utility of transduced N-HBD molecules according to this invention may not require stable expression. Rather, transient expression of the polypeptide may be sufficient for transduced cells to perform their production or delivery function.

Other Therapeutic Compositions

In another embodiment, the N-HBD polypeptide or fusion polypeptide compound of this invention is "therapeutically conjugated" and used to deliver a therapeutic agent to the site to which the compounds home and bind, i.e., tissues or regions rich in heparan sulfates such as tumor sites, tumor metastases or foci of infection/inflammation. The term "therapeutically conjugated" means that the modified N-HBD polypeptide is conjugated to another therapeutic agent that is directed either to the underlying cause or to a "component" of tumor invasion, angiogenesis or inflammation.

Examples of therapeutic radioisotopes useful herein include $^{125}$I, $^{131}$I, $^{90}$Y, $^{67}$Cu, $^{217}$Bi, $^{211}$At, $^{212}$Pb, $^{47}$Sc, and $^{109}$Pd. These atoms can be conjugated to the N-HBD polypeptide compounds directly, indirectly as part of a chelate, or, in the case of iodine, indirectly as part of an iodinated Bolton-Hunter group. The radioiodine can be introduced either before or after this group is coupled to the polypeptide.

Preferred doses of the radionuclide conjugates are a function of the specific radioactivity to be delivered to the target site which varies, in the case of tumors, with tumor type, tumor location and vascularization, kinetics and biodistribution of the N-HBD polypeptide carrier, energy of radioactive emission by the nuclide, etc. Those skilled in the art of radiotherapy can readily adjust the dose of the polypeptide in conjunction with the dose of the particular nuclide to effect the desired therapeutic benefit without undue experimentation. For example, an effective dose of $^{131}$I-N-HBD polypeptide is between about 1 and 1000 μCi per gram of tumor for an extracranial tumor.

Another therapeutic approach included here is the use of boron neutron capture therapy, where a boronated polypeptide is delivered to a desired target site, such as a tumor, most preferably an intracranial tumor (Barth, R F, *Cancer Invest.* 14:534-550 (1996); Mishima, Y. (ed.), *Cancer Neutron Capture Therapy*, New York: Plenum Publishing Corp., 1996; Soloway, A H, et al, (eds), *J. Neuro-Oncol.* 33:1-188 (1997). The stable isotope $^{10}$B is irradiated with low energy (<0.025 eV) thermal neutrons, and the resulting nuclear capture yields a particles and $^7$Li nuclei which have high linear energy transfer and respective path lengths of about 9 and 5 μm. This method is predicated on $^{10}$B accumulation in the tumor with lower levels in blood, endothelial cells and normal tissue (e.g., brain). Such delivery has been accomplished using epidermal growth factor (Yang. W. et al., *Cancer Res* 57:4333-4339 (1997).

Other therapeutic agents which can be coupled to the N-HBD polypeptides according to the method of the invention are drugs, prodrugs, enzymes for activating pro-drugs, photosensitizing agents, gene therapeutics, antisense vectors, viral vectors, lectins and other toxins.

The compositions of the present invention are useful in treating a wide range of diseases and disorders affecting the nervous system, musculature, and epithelia. In addition, these compositions can be used in the treatment of cancer. As used herein, "treatment" encompasses the treatment of an existing disease or condition as well as prophylactic administration prior to detection or manifestation of the disease or condition.

Accordingly, the present invention provides a pharmaceutical composition including a N-HBD fusion polypeptide that is useful in treating any of a variety of diseases or disorders. In one embodiment, a pharmaceutical N-HBD fusion polypeptide composition is employed to treat a mammal. In particular, the composition is useful for treating humans, farm animals (e.g., cows and sheep), zoo animals, animals used in sports (e.g., horses), and pets (e.g., dogs and cats). In a preferred embodiment, the composition is used to treat a human.

A N-HBD fusion polypeptide according to the invention can be useful in promoting the development, maintenance, and/or regeneration of a neuron in vivo.

Two classes of disease or disorder are particularly susceptible to the methods of this invention, based on the knowledge of the effects of NRGs or their antagonists. Described broadly, these include cancer and diseases of the nervous system. The compounds are useful for inhibiting tumor cell invasion and metastasis. Nervous system diseases are preferably neurodegenerative diseases (e.g., Alzheimer's disease, Parkinson's disease, amyotrophic lateral sclerosis (ALS)) stroke, epilepsy, multiple sclerosis (MS), myasthenia gravis, Huntington's chorea, Down's Syndrome, nerve deafness, and Meniere's disease.). Also included are peripheral neuropathies as in diabetes, repair after traumatic injury to the brain or spinal cord.

The present compositions are used to treat a neuropathy, including a peripheral neuropathy which is a disorder affecting the peripheral nervous system, most often manifested as one or a combination of motor, sensory, sensorimotor, or autonomic neural dysfunctions. Examples include, distal sensorimotor neuropathy and autonomic neuropathies, such as reduced gastrointestinal motility or atony of the urinary bladder. Peripheral neuropathies amenable to treatment by the present compositions can be (a) inherited, (b) a result of a systemic disease, or (c) induced by a toxic agent. Examples of hereditary neuropathies are Charcot-Marie-Tooth disease, Refsum's disease, abetalipoproteinemia, Tangier disease, Krabbe's disease, metachromatic leukodystrophy, Fabry's disease, and Dejerine-Sottas syndrome. Examples of neuropathies resulting from systemic disease include post-polio syndrome. Toxic neuropathies include those that are side effects of chemotherapy, e.g., cancer chemotherapy.

The application of the present fusion polypeptides that act as tyrosine kinase receptor antagonists is broad and includes conditions associated with abnormal or undesired angiogenesis or cell migration or invasion. A nonlimiting list of these include primary and metastatic solid tumors, benign hyperplasias, atherosclerosis, myocardial angiogenesis, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions (including psoriasis and scleroderma), lung fibrosis, chemotherapy-induced fibrosis, wound healing with scarring and fibrosis, peptic ulcers, fractures, keloids, and disorders of vasculogenesis, hematopoiesis, ovulation, menstruation, pregnancy and placentation, or any other disease or condition in which angiogenesis is pathogenic or undesired.

In addition to the active EGF-like domain of NRG (as an agonist) and extracellular domains of the erbB receptors (as antagonists), other active growth and differentiation factors and their respective receptors could also be the $P_{trg}$ component of the present fusion polypeptides and could therefore be targeted to cell surfaces as agonists (growth/differentiation factor domains(s) as $P_{trg}$) or antagonists (receptor ECD as $P_{trg}$). This includes, without limit, epidermal growth factor fibroblast growth factors (FGFs), neurotrophins (such as brain derived neurotrophic factor (BDNF) glial derived neurotrophic factor (GDNF), nerve growth factor (NGF), NT4, etc.), VEGF, HB-EGF, and cytokines including but not limited to transforming growth factors α and β (TGFα and TGFβ), netrins, ephrins.

Non-limiting examples of selected nerve growth factors (NGF's) for use in particular neurological disorders are as follows. In ALS, a preferred $P_{trg}$ is BDNF or NT4 which is delivered to HSPG-rich cell surfaces to provide neuroprotection. In Alzheimer's disease, a preferred $P_{trg}$ is any neurotropic factor that stimulates survival or growth of neurons, e.g., central cholinergic neurons. For Parkinson's disease, a preferred $P_{trg}$ is any neurotrophic factor that promotes survival or growth of nigrostriatal dopaminergic neurons (or other dopaminergic cells transplanted to the same site). In myasthenia gravis, the preferred $P_{trg}$ is neuregulin or other stimulator of postsynaptic AChRs delivered to cholinergic neuromuscular junctions. For diabetic neuropathy, a preferred $P_{trg}$ is NGF delivered to any appropriate target organ, such as retina or kidney.

Having now generally described the invention, the same will be more readily understood through reference to the following examples which are provided by way of illustration, and are not intended to be limiting of the present invention, unless specified.

EXAMPLE I

Experimental Procedures

Reagents

Recombinant human NRG polypeptides were provided by AMGEN (Thousand Oaks, Calif.). The isolated EGF-like domain corresponds to amino acids 177-246, and the IG-EGF domain corresponds to amino acids 14-246 both of the human β1 form expressed in *E. coli* (FIG. 1) and used previously (Loeb et al., 1995, supra). Heparin (porcine intestinal mucosa, ~13,000 Mr) and bovine serum albumin (BSA, Fraction V) were purchased from Sigma Chemical Co. (St. Louis, Mo.). Heparitinase and Chondroitinase ABC were purchased from Seikagaku Corp. (Japan). The tyrosine kinase inhibitor tyrphostin AG1478 was purchased from CalBiochem (La Jolla, Calif.). All other tissue culture reagents were purchased from Invitrogen-Life Technologies (Carlsbad, Calif.).

Chick Myotube Cultures

Chick myotube cultures from embryonic day 11 pectoral muscle were cultured on 50 μg/ml collagen type I from rat tail (Collaborative Biomedical Products) as described previously (18). 2% CEE media was made from 2% chick embryo extract (CEE), 10% horse serum, 1% penicillin/streptomycin, 1% Glutamine and 1% pyruvate in MEM. Cells were plated at 60,000 cells per 48-well tissue culture plate in 300 μl media and at $3 \times 10^5$ cells/dish in 2 ml media in 35 mm tissue culture dishes and kept in a 5% $CO_2$ incubator. Fresh 2% CEE media was changed on the $4^{th}$ day after plating and experiments were done on the $7^{th}$ day after plating.

Western Blot for p185 Receptor Phosphorylation

Each form of NRG with and without other reagents was applied to 7 day-old chick myotubes for 45 min at 37° C. The medium was then discarded, and the cells were solubilized in SDS sample buffer and boiled for 5 min as described (Corfas et al., supra). Phosphorylated forms of the erbB receptors (p185) were detected by western blot analysis using the phosphotyrosine monoclonal antibody ("mAb") PY 20 (Transduction laboratories) after first resolving on overrun 5% reducing SDS-Polyacrylamide gels. The filters were then probed with a goat anti-mouse IgG coupled to peroxidase (Boehringer Mannheim Corp.) and exposed to X-blue film (Kodak) after treatment with chemiluminescence reagents (Dupont-NEN).

Competitive Binding Assay of $^{125}$I-NRG $^{125}$I-IG-EGF NRG was prepared (Hunter, W M et al., (1964) *Biochem J* 91, 43-56) using the Chloramine-T method yielding a specific activity of 9,000 Ci/nmol. Chick myotube cultures were pretreated with either heparitinase (0.04 U/ml, to remove endogenous heparan sulfates) or chondroitinase (0.04 U/ml, to remove chondroitin sulfates) for 90 min at 37°. $^{125}$I-IG-EGF, 0.1 nM, was applied to pre-chilled myotube cultures in quadruplicates for 2 hrs on ice without or with 1 μM cold ligand (IG-EGF) or 500 μg/ml soluble heparin. Total cpm bound was measured in a gamma counter (Packard Instruments) after washing three times with cold MEM containing 0.1% BSA and total cpm bound was measured after solubilization in 100 μl of 1N NaOH, 0.5 mg/ml deoxycholate for 10 min. at room temperature.

AChR Insertion Rate and Northern Blot Analysis

Measurement of newly inserted AChR proteins in the myotube membrane was achieved by blocking AChR binding sites with cold α-bungarotoxin, allowing newly synthesized AChRs to appear in the plasma membrane, and then measuring these new AChRs with [$^{125}$I]α-bungarotoxin (Amersham) as described previously (Falls, D L et al., (1993) *Cell* 72, 801-815). Northern blots were performed on RNA extracted from either 35 mm plates or pooled wells from 48-well plates using Ultraspec (Biotecx laboratories, Inc., Houston, Tex.) as described previously (Loeb, J A et al., (1997) *J Neurosci* 17, 1416-1424). AChR α subunit exon 7 and flanking sequence in vector pBluescript was provided by Dr. Jakob Schmidt in SUNY and $^{32}$P labeled probes were prepared from this 399 bp fragment by random priming using Prime It II kit (Stratagene, La Jolla, Calif.). The membrane was re-probed with a $^{32}$P labeled GAPDH probe for normalization purposes.

Quantitative Analysis

Quantitation was performed either using a phosphorimager (Molecular Dynamics) or by image analysis of X-ray films on non-saturated images after scanning with a Power Look (UMAX) flat bed scanner with transparency adapter, and then analyzing with Metamorph Imaging system version 4.0 (Universal Imaging Corporation). Relative mRNA levels were normalized to GAPDH levels.

EXAMPLE II

Figure 2:
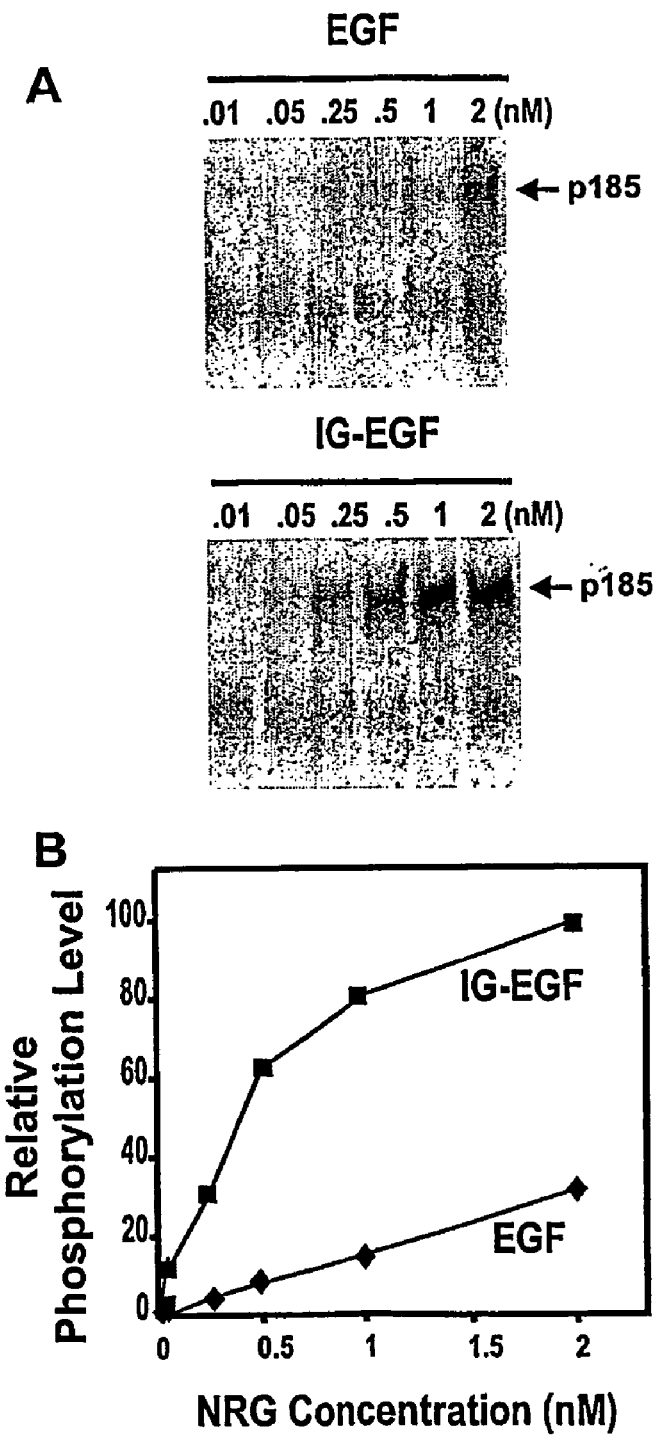
FIGS. 2A and 2B is a series of graphs showing that the IG domain increases the potency of receptor phosphorylation. The results described in FIG. 2A are from a study in which increasing concentrations of either the EGF or the IG-EGF construct was applied to chick myotube cultures for 45 min. Receptor phosphorylation activity was measured by western blot analysis using anti-phosphotyrosine antibodies. The activated NRG receptor complex appeared as a diffuse band at approximately 185 kDa, labeled as p185, which includes phosphorylated forms of erbB2, erbB3 and erbB4. At the same concentrations, the NRG construct with the IG-like domain induced more receptor phosphorylation than did the EGF-like domain alone. Shown in FIG. 2B are quantitative measurements demonstrated the IG-EGF form was 4-fold more potent than the EGF domain alone. Results were normalized to the maximal response with the IG-EGF form set at 100%.

The Neuregulin HBD Increases the Potency of the EGF-Like Domain through HSPG Interactions In order to assess the contribution the N-HBD of NRG makes on erbB receptor phosphorylation, we compared the potency of recombinant NRG forms with (IG-EGF) and without (EGF) the N-HBD on primary chick myotube cultures. There are biologically active, recombined NRG Type I β1 isoforms that we have used previously (Loeb et al., 1995, supra (see FIG. 1). Although there are some additional sequences besides the N-HBD on the IG-EGF construct, the heparin-binding portion has been localized to the N-HBD (Meier et al., supra). After treatment with NRG, the erbB receptor complex appeared as a diffuse band at approximately 185 kDa called "p185" that included phosphorylated forms of erbB2, erbB3, and erbB4 on phosphotyrosine western blot. Employing equal molar amounts, the IG-EGF form was 4-fold more potent than the EGF form alone during the 45 minute assay (FIGS. 2A, 2B).

The present inventor investigated the possibility that this increase in potency of the IG-EGF form is due to HSPG interactions on the myotube surface. The proportion of NRG that binds to HSPGs versus erbB receptors was compared by selectively removing endogenous HSPGs with heparitinase. A competitive binding study of $^{125}$I-NRG (IG-EGF) demonstrated that NRG is distributed fairly equally between both erbB receptors and endogenous HSPGs (FIG. 3A). Specific binding, assessed by blocking with cold IG-EGF NRG, was about 25% of total binding. Similarly, removing endogenous heparan sulfates reduced total binding by 25%, but did not reduce the specific binding to erbB receptors. Soluble heparin blocked total binding by 50%, similar to the combination of heparitinase and cold NRG. This suggested that a similar proportion of $^{125}$I-NRG was associated with its receptor and with endogenous HSPGs. Pre-treatment with an enzyme that selectively degrades chondroitin sulfate (chondroitinase) had no effect on binding to either erbB receptors or HSPGs demonstrating the specificity of NRG interactions with endogenous HSPGs.

The next study examined whether this increased potency of the IG-EGF form on receptor phosphorylation was due directly to interactions with endogenous HSPGs (FIG. 3B). While treatment with heparitinase had no effect on EGF-like domain induced receptor phosphorylation, it reduced erbB phosphorylation induced by the IG-EGF form to the same level as the EGF-like domain alone. This result suggested that interactions between the N-HBD of NRG and endogenous HSPGs are directly responsible for the increased potency. This experiment also suggested that the two recombinant ligands were correctly folded, since their activity is the same in the absence of HSPGs.

EXAMPLE III

Soluble Heparin has Different Effects on NRG-Induced Receptor Phosphorylation and Induction of AChR Proteins Adding soluble heparin both stimulates and inhibits heparin-binding growth factors. FIG. 3A shows that high concentrations of soluble heparin effectively blocked NRG's ability to bind to its receptor. Studies were done to explore the effects of soluble heparin both in modulating NRG's ability to stimulate erbB receptor phosphorylation and AChR synthesis in cultured myotubes. Whereas heparin had no effect on receptor phosphorylation induced by the EGF-like domain, as little as 5 μg/ml heparin almost completely blocked receptor phosphorylation (p185) with the NRG form containing the N-HBD (FIG. 4A).

Even though heparin inhibited receptor phosphorylation at all concentrations above 1.0 μg/ml, AChR induction responded to heparin in a biphasic manner. At high concentrations, heparin was inhibitory, while lower concentrations, up to 10 μg/ml, stimulated the rate of appearance of newly inserted AChR proteins onto the muscle membrane (FIG. 4B). Given the relative time course of these two assays, the results suggested that the stimulatory effects of low concentrations of heparin occurred as a result of the longer course of this assay.

EXAMPLE IV

The Neuregulin HBD Enhances AChR mRNA and Protein Expression by Maintaining erbB Receptor Phosphorylation Thus far, these results suggested that the N-HBD concentrated NRG along cell surfaces through HSPG interactions and that this concentration may be responsible for increased NRG potency for receptor binding and phosphorylation.

Another potential function of this interaction is to provide sustained signaling. The next experiment examined the time of NRG exposure required to induce AChR mRNA and protein expression. AChR induction was measured after treating myotubes for different intervals from 15 min to 24 hrs with the same concentration of NRG (EGF vs. IG-EGF) followed by "washing out" of the NRG. AChR mRNA levels were then measured (FIGS. 5A, 5B) and new surface proteins (FIG. 5C) 24 hrs from the start. The AChR a subunit was measured by northern blot analysis and compared to the housekeeping gene GAPDH to normalize the data. The α subunit was chosen because this subunit has been shown previously to have the greatest induction by NRG in chick myotubes (Altiok et al., supra; Harris, D. A. et al. (1988) *Proc Natl Acad Sci USA* 85, 1983-1987). While maximal activation of AChR mRNA expression by the IG-EGF domain was achieved with a 15 min treatment, 24 hrs were needed for the EGF-like domain to induce significant AChR mRNA expression. Similarly, a significant lag of more than 8 hrs was required for the EGF-like domain to evoke a similar response as did the IG-EGF form in promoting the insertion of new AChR proteins on the cell surface (FIG. 5C). From the earlier results, it is concluded that the IG-like domain binds to endogenous HSPGs so that the IG-EGF form is not in fact "washed out" in this assay, but provides a steady source of ligand to activate the erbB receptors. Unexpectedly, the appearance of new AChR proteins on the cell surface preceded the increase in mRNA, suggesting that mechanisms that increase AChR mRNA and protein expression on the cell surface may be distinct.

The next experiment examined the phosphorylation state of the erbB receptors for 24 hrs of NRG exposure (FIG. 6A). Consistent with results in FIGS. 2A, 2B, the initial phosphorylation response was greater with IG-EGF than EGF for the first 2 hrs. However, after 2 hrs, both constructs kept the erbB receptors phosphorylated at similar, lower level through 24 hrs. The level of phosphorylation at 24 hrs was significantly above background without NRG treatment as seen in the blank lane. When "wash out" of these constructs was done after 45 min of treatment, and p185 phosphorylation was measured at indicated time points (FIG. 6B), the response induced by the EGF-like domain decayed rapidly and was lost within 1 hr after the wash. In contrast, the IG-EGF construct kept the erbB receptors phosphorylated for a full 8 hrs after the wash. These results suggested that sustained activation of erbB receptors is a consequence of NRG-HSPG interactions and may be required for AChR mRNA and protein induction.

Finally, in order to demonstrate the importance of sustained erbB receptor phosphorylation in AChR induction, a specific erbB tyrosine kinase inhibitor AG1478 (Levitzki, A. et al., (1995) *Science* 267, 1782-1788) was used to block erbB receptor phosphorylation at specific times after adding NRG (FIG. 7A-7C). FIG. 7A shows that the concentration of inhibitor required to completely block erbB receptor phosphorylation using the EGF construct was above 1 µM. In studies using 10 µM AG 1478 shown in FIGS. 7B and 7C, it was observed that 12-24 hrs of sustained receptor phosphorylation were necessary for the EGF-like domain to increase AChR mRNA levels, suggesting a need for sustained receptor phosphorylation. Similar results were obtained using the IG-EGF construct of NRG, however, higher concentrations of the inhibitor were required.

Discussion of Results in Examples II-IV

The studies presented above examined how extracellular interactions between the N-HBD and HSPGs in the ECM modulate the intracellular signaling events that regulate the expression of synaptic AChRs. These studies demonstrated both short- and long-term effects of NRG-HSPG interactions. The addition of the IG-like domain to the EGF-like domain of NRG resulted in a rapid and transient increase in erbB receptor phosphorylation that required interactions with endogenous HSPGs. Sustained NRG-erbB receptor activation, however, was required to turn on AChR mRNA and protein expression. These results indicated that the IG-like domain is needed to keep sufficiently high concentrations of the EGF-like domain near the erbB receptors for a sufficient duration required for induction of AChR gene expression.

During embryonic development, HSPGs and NRG become concentrated coincidentally in the synaptic basal lamina of neuromuscular junctions and remain there throughout adult life (Loeb et al., 1999). Our observation that sustained erbB receptor activation is required to induce AChR expression may be the reason why such high concentrations of NRG are maintained in the synaptic basal lamina.

The present results demonstrated that more than 8 hrs of receptor activation was needed to induce AChR mRNA and protein expression and that this receptor activation required the continuous presence of NRG. Earlier studies showed that more than 5 hrs of NRG exposure was required to increase the insertion rate of new AChRs (Buc-Caron, M. H. et al., (1983) *Dev Biol* 95, 378-386) and up to 12 his exposure was needed to increase voltage-gated sodium channels in chick muscle cultures (Corfas et al., supra). The present results differ considerably from a recent report where as little as a one minute exposure of the EGF-like domain of NRG was needed to induce AChR mRNA 24 hrs after addition to C2C12 cells (Si, J. et al., (1999) *J Neurosci* 19, 8498-8508). While the difference could be due to the different myotube culture systems used, it is also possible that the other investigators did not "wash away" the NRG. As reported here, when the chick myotube cultures were washed with PBS instead of serum containing media, similar results were obtained in that both the EGF and the IG-EGF induced AChR mRNA after 24 hrs after only brief (15 min) exposure.

It is concluded herein that the reason the ligand is required for over 8 hrs is because the erbB receptors need to be maintained in a phosphorylated state for this entire period in order to increase AChR mRNA. This was proved using a specific tyrosine kinase antagonist added at different times after NRG addition. It is not clear why sustained erbB receptor activation is needed. There are, however, examples from the literature where sustained activation of tyrosine kinase signaling pathways such as MAPK and CREB for 4 hrs or more are needed to induce cell differentiation, migration and the expression of specific genes (Liu, F. C. et al., (1996) *Neuron* 17, 1133-1144; Marshall, C J et al., (1995) *Cell* 80, 179-185; McCawley, L J et al., (1999) *J Biol Chem* 274, 4347-4353).

Sustained receptor activation may be needed to recruit other kinases and/or transcription factors or perhaps is needed to initiate new protein synthesis. Si et al., supra, showed that new protein synthesis was needed to induce AChR gene transcription. In that report, newly-made c-JUN and/or c-FOS mRNA were required to mediate the up-regulation of AChR mRNA by NRG. Pretreatment of C2C12 cells with a protein synthesis inhibitor, cycloheximide, blocked NRG-induced AChR α-subunit mRNA completely suggesting that de novo protein synthesis was needed.

There are a growing number of growth and differentiation factors that bind to ECM HSPGs including NRG, acidic and basic FGFs, transforming growth factor-β (TGF-β), granulocyte-macrophage colony-stimulating factor, interleukin-3, interferon γ, the netrins, heparin-binding epidermal growth factor (Schlessinger et al., supra; Ruoslahti, E. et al., (1991) *Cell* 64, 867-869; Serafini, T. et al., (1994) *Cell* 78, 409-424). Interactions with ECM HSPGs are thought to provide a readily accessible store of factors, to protect them from proteolytic degradation, and in some instances, to play important regulatory roles in their functions. FGF is one of the best studied growth factors in which heparin or HSPG binding is necessary for receptor dimerization and activation (Shlessinger et al., supra; Schlessinger, J. (2000) *Cell* 103, 211-225). For other growth factors, such as TGF-β, heparin-binding EGF and NRG, receptor dimerization can be achieved in the absence of soluble heparin or cell surface HSPGs, but HSPGs may function to enhance the biological activity of these growth factors (Higashiyama, S. et al., (1993) *J Cell Biol* 122, 933-940). IT was shown above that a similar proportion of NRG associates with its receptors and with endogenous HSPGs on the cell surface. As a result of this interaction, NRG-induced activation of erbB receptor phosphorylation was increased by 4-fold. Removing endogenous HSPGs by heparitinase treatment eliminated this increase in potency. A similar observation was described for the L6 muscle cell line (Han and Fischbach, (2000) Soc. Neurosci. Abs.25:43).

There are a number of possible explanations as to why HSPGs increases NRG potency. The most likely is that endogenous HSPGs situated on the cell surface concentrate NRG in a microenvironment near erbB receptors, thus increasing the local ligand concentration. In addition, the HSPGs may present NRG molecules to their higher affinity erbB receptors. Finally, heparan sulfate may simultaneously bind to several NRG monomers producing a multimer of ligands that could more effectively stimulate multimeric receptor activation. Similar mechanisms have been proposed for FGF, where additional interactions between HSPGs and the FGF receptor have been proposed (Schlessinger, 2000, supra).

The Examples described the effects of soluble heparin on NRG-induced receptor phosphorylation and AChR expression. It was shown that that while soluble heparin blocked NRG binding and NRG-induced erbB receptor phosphorylation, soluble heparin had a biphasic effect on AChR protein expression. Specifically, high concentrations of heparin blocked AChR protein expression, whereas low concentrations actually stimulated new AChR protein expression. Similar biphasic effects of soluble heparin have been described for FGF (Krufka, A. et al., (1996) *Biochemistry* 35, 11131-11141).

One possible explanation for the present observations is that low concentrations of soluble heparin release NRG from endogenous HSPG binding sites, thus freeing it to interact with the high-affinity erbB receptors. High concentrations of heparin, on the other hand, not only free NRG from endogenous HSPGs, but also keep it away from cell surface erbB receptors.

One of the more surprising results here was that even though both AChR mRNA and protein expression required prolonged NRG exposure, new AChR protein expression preceded the rise in AChR mRNA. This observation suggested that the cell-signaling mechanism that increases the insertion of new AChRs on the cell surface is distinct from the mechanism that increases AChR mRNA. Further experiments will sort out this apparent dissociation between AChR mRNA and protein expression that may involve different signaling pathways initiated by erbB receptor activation. Some of the earlier signaling events that do not require protein synthesis may promote the movement of pre-existing AChRs to the cell surface, whereas in order to make new AChR mRNA, more prolonged signaling is required (e.g., the requirement for new protein synthesis (see Si et al., supra.

EXAMPLE V

Addition of the HBD to Other Proteins Increases Their Activities

A fusion protein of the N-HBD fused to the extracellular domain of the erbB4 (tyrosine kinase receptor for EGF), shown schematically in FIG. 8A, was produced by standard recombinant DNA methods. This product is designated "HBDB4HA" and includes an epitope tag (hemagglutinin, "HA") which is commercially available. This construct was tested for its ability to inhibit the NRG-induced Tyr phosphorylation of erbB4. The control antagonist was a fusion of erbB4 extracellular domain and the HA tag. The tag was included for convenience during purification.

These antagonists were tested for their ability to inhibit agonist-induced tyrosine phosphorylation induced by two NRG forms: IG-EGF, which includes the HBD, and the EGF domain, which does not. Agonists or mixtures of agonist and antagonist were incubated with L6 muscle cells for 40 min., after which the cells were lysed, and the lysates run on 5% SDS gels. The gels were stained with a commercial anti-phospho-Tyr antibody. This is described in Example I and II. As noted in Example II, the erbB receptor complex appeared as a diffuse band at approximately 185 kDa called "p185" that included phosphorylated forms of erbB2, erbB3, and erbB4 on phosphotyrosine western blot. The western blots are shown in FIG. 8C and the relative amount of phospho-Tyr is shown in the graph of FIG. 8B.

The results show that the fusion of the HBD confers increased antagonist activity on the soluble erbB4 protein (HBDB4HA group) in blocking the tyrosine phosphorylation of the erbB receptors induced by NRG compared to a construct that lacks the HBD (B4HA). This was observed using two forms of NRG: that which included the HBD ("IG-EGF") and that which did not include the HBD ("EGF"). Thus, by combining the N-HBD to another protein, it is possible to increase that protein's binding activity and biological effect.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A fusion polypeptide comprising (a) a first targeting polypeptide that binds heparan sulfate when said fusion polypeptide is permitted to contact cells or tissues, thereby localizing the fusion polypeptide to said heparan-sulfate rich cell or tissue surface;

wherein said fusion polypeptide binds to heparin or to a heparan sulfate proteoglycan when measured in a conventional heparin-binding or heparan-sulfate binding assay, which first targeting polypeptide consists of:

(i) a human neuregulin heparin-binding domain (N-HBD) the sequence of which is SEQ ID NO:1; or (ii) a heparin-binding fragment thereof the sequence of which is KWFKNGNELNRKNKPQNIKIQKKPGK (SEQ ID NO: 7); or (iii) a heparin binding fragment the sequence of which is K-x-x-K-x-x-x-x-x-x-R-K-x-K-x-x-x-x-K-x-x-K-K-x-x-K (SEQ ID NO:10), wherein x is any amino acid; and (b) a second targeted polypeptide $P_{trg}$ that is to be targeted and localized to the heparan sulfate-rich cell or tissue surface which second polypeptide is neuregulin (NRG), the extracellular domains of an erbB receptor, epidermal growth factor (EGF), a fibroblast growth factor (FGF), nerve growth factor (NGF) or a neurotrophic factor;

wherein said fusion polypeptide, through the action of said $P_{trg}$, has enhanced biological activity in stimulating or blocking a target receptor compared to native $P_{trg}$ or $P_{trg}$ not fused to said first targeting polypeptide.

2. The fusion polypeptide of claim 1 wherein said first targeting polypeptide is fused directly to the second targeted polypeptide.

3. The fusion polypeptide of claim 1 wherein the first targeting polypeptide is said heparin binding fragment the sequence of which is SEQ ID NO: 7.

4. The fusion polypeptide of claim 1 wherein the first targeting polypeptide is said heparin-binding fragment the sequence of which is K-x-x-K-x-x-x-x-x-x-R-K-x-K-x-x-x-K-x-x-K-K-x-x-K (SEQ ID NO:10), wherein x is any amino acid.

5. The fusion polypeptide of claim 1 that further comprises a linker peptide VPRGSD (SEQ ID NO:11) or DDKDWH (SEQ ID NO:12) between the first targeting polypeptide and the second targeted polypeptide.

6. A tandemly linked dimer or trimer of the fusion polypeptide of claim 1.

7. The fusion polypeptide of claim 1 wherein said second targeted polypeptide $P_{trg}$ is an extracellular domain of an erbB receptor.

8. The fusion polypeptide of claim 1 wherein said second targeted polypeptide $P_{trg}$ is an epidermal growth factor or a neurotrophic factor.

9. The fusion polypeptide of claim 1 wherein said neurotrophic factor is neurotrophin, brain derived neurotrophic factor (BDNF), or glial derived neurotrophic factor (GDNF).

10. The fusion polypeptide of claim 1 wherein the first targeting polypeptide is said human N-HBD, the sequence of which is SEQ ID NO: 1.

11. A method for localizing a targeted polypeptide to a cell or tissue surface rich in heparan sulfate, and thereby enhancing the polypeptide's biological activity at said surface, comprising providing to said surface the fusion polypeptide of claim 1, whereby the $P_{trg}$ of the fusion polypeptide is localized to said surface, such that the biological activity of the $P_{trg}$ is increased compared to the activity of (i) native $P_{trg}$ or (ii) $P_{trg}$ that is not fused to said targeting polypeptide.

12. The method of claim 11 wherein said providing is in vivo.

* * * * *

SEQUENCE LISTING

```
<160> NUMBER OF SEQ ID NOS: 12

<210> SEQ ID NO 1
<211> LENGTH: 70
<212> TYPE: PRT
<213> ORGANISM: Homo sapiens

<400> SEQUENCE: 1

Gly Ser Lys Leu Val Leu Arg Cys Glu Thr Ser Ser Glu Tyr Ser Ser
1               5                   10                  15

Leu Arg Phe Lys Trp Phe Lys Asn Gly Asn Glu Leu Asn Arg Lys Asn
```

```
                    20                  25                  30

Lys Pro Gln Asn Ile Lys Ile Gln Lys Lys Pro Gly Lys Ser Glu Leu
            35                  40                  45

Arg Ile Asn Lys Ala Ser Leu Ala Asp Ser Gly Glu Tyr Met Cys Lys
        50                  55                  60

Val Ile Ser Lys Leu Gly
65                  70

<210> SEQ ID NO 2
<211> LENGTH: 70
<212> TYPE: PRT
<213> ORGANISM: Rattus sp.

<400> SEQUENCE: 2

Gly Ser Lys Leu Val Leu Arg Cys Glu Thr Ser Ser Glu Tyr Ser Ser
1               5                   10                  15

Leu Arg Phe Lys Trp Phe Lys Asn Gly Asn Glu Leu Asn Arg Lys Asn
                20                  25                  30

Lys Pro Glu Asn Ile Lys Ile Gln Lys Lys Pro Gly Lys Ser Glu Leu
            35                  40                  45

Arg Ile Asn Lys Ala Ser Leu Ala Asp Ser Gly Glu Tyr Met Cys Lys
        50                  55                  60

Val Ile Ser Lys Leu Gly
65                  70

<210> SEQ ID NO 3
<211> LENGTH: 70
<212> TYPE: PRT
<213> ORGANISM: Avian sp.

<400> SEQUENCE: 3

Gly Gln Lys Leu Val Leu Arg Cys Glu Thr Thr Ser Glu Tyr Pro Ala
1               5                   10                  15

Leu Arg Lys Trp Leu Lys Asn Gly Lys Glu Ile Thr Lys Lys Asn Arg
                20                  25                  30

Pro Glu Asn Val Lys Ile Pro Lys Lys Gln Lys Lys Tyr Ser Glu Leu
            35                  40                  45

His Ile Tyr Arg Ala Thr Leu Ala Asp Ala Gly Glu Tyr Ala Cys Arg
        50                  55                  60

Val Ser Ser Lys Leu Gly
65                  70

<210> SEQ ID NO 4
<211> LENGTH: 210
<212> TYPE: DNA
<213> ORGANISM: Homo sapiens

<400> SEQUENCE: 4
ggttccaaac tagtccttcg gtgtgaaacc agttctgaat actcctctct cagattcaag      60
tggttcaaga atgggaatga attgaatcga aaaacaaac cacaaaatat caagatacaa      120
aaaaagccag ggaagtcaga acttcgcatt aacaaagcat cactggctga ttctggagag    180
tatatgtgca aagtgatcag caaattagga                                       210

<210> SEQ ID NO 5
<211> LENGTH: 210
<212> TYPE: DNA
<213> ORGANISM: Rattus sp.
```

-continued

```
<400> SEQUENCE: 5
ggctccaagc tagtgctccg gtgcgaaacc agctccgagt actcctcact cagattcaaa      60
tggttcaaga atgggaacga gctgaaccgc aaaataaac cagaaaacat caagatacag      120
aacaagccag ggaagtcaga gcttcgaatt aacaaagcat ccctggctga ctctggagag     180
tatatgtgca aagtgatcag caagttagga                                      210

<210> SEQ ID NO 6
<211> LENGTH: 213
<212> TYPE: DNA
<213> ORGANISM: Avian sp.

<400> SEQUENCE: 6
ggtcagaagc tagtgctaag gtgtgaaacc acttcagagt accctgcgct cagattcaaa     60
tggttaaaga acgggaagga ataacgaaa aaaacagac ccgaaaatgt caagatcccc      120
aaaaagcaaa agaaatactc tgagcttcat atttatagag ccacgttggc tgacgctggg    180
gaatacgcat gcagagtgag cagcaaacta ggg                                  213

<210> SEQ ID NO 7
<211> LENGTH: 26
<212> TYPE: PRT
<213> ORGANISM: Homo sapiens

<400> SEQUENCE: 7

Lys Trp Phe Lys Asn Gly Asn Glu Leu Asn Arg Lys Asn Lys Pro Gln
1               5                  10                  15

Asn Ile Lys Ile Gln Lys Lys Pro Gly Lys
            20                  25

<210> SEQ ID NO 8
<211> LENGTH: 26
<212> TYPE: PRT
<213> ORGANISM: Rattus sp.

<400> SEQUENCE: 8

Lys Trp Phe Lys Asn Gly Asn Glu Leu Asn Arg Lys Asn Lys Pro Glu
1               5                  10                  15

Asn Ile Lys Ile Gln Lys Lys Pro Gly Lys
            20                  25

<210> SEQ ID NO 9
<211> LENGTH: 26
<212> TYPE: PRT
<213> ORGANISM: Avian sp.

<400> SEQUENCE: 9

Lys Trp Leu Lys Asn Gly Lys Glu Ile Thr Lys Lys Asn Arg Pro Glu
1               5                  10                  15

Asn Val Lys Ile Pro Lys Lys Gln Lys Lys
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: Xaa can be any amino acid
```

```
<220> FEATURE:
<221> NAME/KEY: MISC_FEATURE
<222> LOCATION: (5)..(10)
<223> OTHER INFORMATION: Xaa can be any amino acid
<220> FEATURE:
<221> NAME/KEY: MISC_FEATURE
<222> LOCATION: (13)..(13)
<223> OTHER INFORMATION: Xaa can be any amino acid
<220> FEATURE:
<221> NAME/KEY: MISC_FEATURE
<222> LOCATION: (15)..(17)
<223> OTHER INFORMATION: Xaa can be any amino acid
<220> FEATURE:
<221> NAME/KEY: MISC_FEATURE
<222> LOCATION: (19)..(20)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid

<400> SEQUENCE: 10

Lys Xaa Xaa Lys Xaa Xaa Xaa Xaa Xaa Xaa Arg Lys Xaa Lys Xaa Xaa
1               5                   10                  15

Xaa Lys Xaa Xaa Lys Lys Xaa Xaa Lys
            20                  25

<210> SEQ ID NO 11
<211> LENGTH: 6
<212> TYPE: PRT
<213> ORGANISM: Artificial Sequence
<220> FEATURE:
<223> OTHER INFORMATION: Linker for fusion polypeptide

<400> SEQUENCE: 11

Val Pro Arg Gly Ser Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Linker for fusion polypeptide

<400> SEQUENCE: 12

Asp Asp Lys Asp Trp His
1               5
```